United States Patent
Yoshinaga et al.

[11] Patent Number: 6,104,195
[45] Date of Patent: *Aug. 15, 2000

[54] APPARATUS FOR DETECTING A CONDITION OF BURNING IN AN INTERNAL COMBUSTION ENGINE

[75] Inventors: Tohru Yoshinaga, Okazaki; Tokio Kohama, Nishio; Hiroshi Yorita, Kariya; Yasuyuki Satou, Aichi-ken; Masao Kano, Gamagoori; Toshiaki Yamaura, Anjo, all of Japan

[73] Assignees: Denso Corporation, Kariya; Nippon Soken Inc., Nishio, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 08/832,201

[22] Filed: Apr. 8, 1997

Related U.S. Application Data

[63] Continuation-in-part of application No. 08/642,420, May 3, 1996, abandoned.

[30] Foreign Application Priority Data

| May 10, 1995 | [JP] | Japan | 7-137377 |
| Mar. 4, 1996 | [JP] | Japan | 8-75215 |
| Apr. 8, 1996 | [JP] | Japan | 8-085044 |

[51] Int. Cl.[7] .............................. F02P 17/12; G01N 27/62
[52] U.S. Cl. .................. 324/459; 324/392; 73/23.31; 73/35.08; 73/116
[58] Field of Search .................. 123/425, 481; 73/35, 116, 23.31, 35.08; 324/399, 459, 391, 392, 393, 464

[56] References Cited

U.S. PATENT DOCUMENTS

| 4,608,855 | 9/1986 | Baluhut | 73/35 |
| 4,648,367 | 3/1987 | Gillbrand | 123/425 |

(List continued on next page.)

FOREIGN PATENT DOCUMENTS 58-007536   1/1983   Japan .

(List continued on next page.)

*Primary Examiner*—Glenn W. Brown
*Attorney, Agent, or Firm*—Pillsbury Madison & Sutro LLP

[57] ABSTRACT

An apparatus for detecting a condition of burning in an internal combustion engine includes a pair of opposed electrodes provided in a combustion chamber of the engine, and an AC voltage applying device for applying an AC voltage between the opposed electrodes. A current detecting device is operative for detecting a current flowing between the opposed electrodes. A current generating means for generating a current-representing signal depending on the detected current, the current generating means having a differentiating circuit for differentiating the AC voltage into the capacitance-current representing signal. In another aspect of this invention, the apparatus further comprises calculating means for calculating ratios between a parameter represented by the burning-ion current representing signal and a parameter represented by a signal depending on the AC voltage applied between the opposed electrodes. A waveform processing device is operative for removing the capacitive current component from the current-representing signal to extract a burning ion current component, and for generating a burning-ion-current representing signal depending on the extracted burning ion current component. The capacitive current component occurs in correspondence with the AC voltage. One aspect of the invention utilizes calculating means for calculating a ratio between a parameter represented by the burning-ion-current representing signal and a parameter represented by a signal depending on the AC voltage applied between opposed electrodes. The burning ion current component corresponds to a burning ion current which flows between the opposed electrodes. A burning condition detecting device is operative for detecting a condition of burning in the combustion chamber of the engine on the basis of the burning-ion-current representing signal generated by the waveform processing device. The waveform processing device includes an integration processing device for integrating the current-representing signal to generate the burning-ion-current representing signal.

22 Claims, 17 Drawing Sheets

U.S. PATENT DOCUMENTS

| | | | |
|---|---|---|---|
| 4,672,324 | 6/1987 | van Kampen | 328/6 |
| 5,180,984 | 1/1993 | Murata | 324/399 |
| 5,207,200 | 5/1993 | Iwata | 123/425 |
| 5,239,973 | 8/1993 | Murata | 123/635 |
| 5,263,452 | 11/1993 | Ohsawa et al. | 123/425 |
| 5,272,914 | 12/1993 | Murata | 73/116 |
| 5,343,844 | 9/1994 | Fukui | 123/481 |
| 5,396,176 | 3/1995 | Ishii et al. | 324/388 |
| 5,503,132 | 4/1996 | Miyata | 123/630 |
| 5,510,715 | 4/1996 | Takeuchi | 324/391 |
| 5,675,072 | 10/1997 | Yasuda | 73/35.08 |
| 5,701,077 | 12/1997 | Inagaki | 324/399 |
| 5,701,876 | 12/1997 | Morita | 123/630 |
| 5,778,855 | 7/1998 | Czekala | 123/416 |
| 5,925,819 | 7/1999 | Yoshinaga et al. | 73/117.3 |

FOREIGN PATENT DOCUMENTS

| | | |
|---|---|---|
| 62-071581 | 3/1988 | Japan . |
| 5-044624 | 2/1993 | Japan . |
| 5-087036 | 4/1993 | Japan . |
| 5-149230 | 6/1993 | Japan . |

FIG. 7
(D)
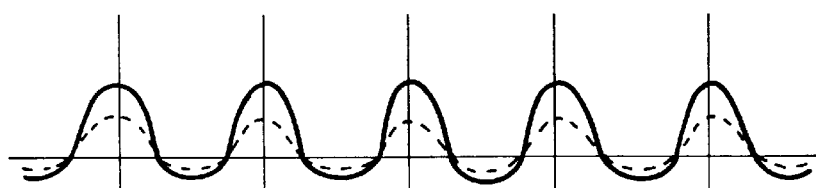
(E)
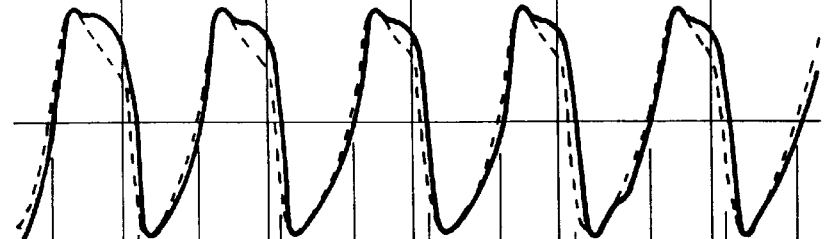
(F)
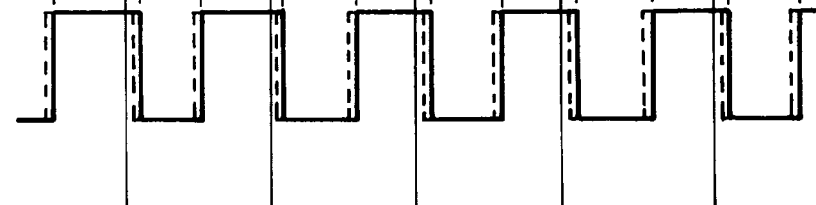
TIME →

APPARATUS FOR DETECTING A CONDITION OF BURNING IN AN INTERNAL COMBUSTION ENGINE

CROSS-REFERENCES TO RELATED APPLICATIONS

This is a continuation-in-part of U.S. patent application, Ser. No. 08/642,420, filed on May 3, 1996, now abandoned.

BACKGROUND OF THE INVENTION

1. Field of the Invention

This invention relates to an apparatus for detecting a condition of burning in an internal combustion engine.

2. Description of the Related Art

It is known to control a spark timing in an internal combustion engine in response to a knock condition thereof. Generally, such knock control uses a sensor for detecting engine vibration as an indication of an engine knock condition. However, engine vibration is caused by not only knock but also other factors. The vibration-based knock sensor tends to output an inaccurate signal when engine vibration is caused by a factor other than knock.

Japanese published unexamined patent application 58-7536 discloses that the ion current, which is generated between the electrodes of an engine ignition plug due to detonation waves, is detected by an ion current sensor. The output signal of the ion current sensor has an amplitude and a width which vary with the intensity of generated engine knocking. Therefore, the occurrence of the knocking and the intensity of the knocking are detected directly and accurately without recognizing the vibration of the engine as the knocking.

U.S. Pat. No. 4,672,324 discloses a flame protection circuit having a first input terminal for a flame probe and a second input terminal for a burner bed. The circuit in U.S. Pat. No. 4,672,324 includes an alternating voltage source and a parallel-combination of a resistor and a capacitor connected to the input terminals. In the presence of a flame between the burner bed and the flame probe, an ionization current flow has a direct current component because of the rectifying effect of the flame. The direct current component produces a measuring direct voltage across the capacitor. The circuit further includes a comparator which compares the measuring direct voltage with a reference voltage to produce a final output signal. The final output signal represents whether or not the flame is present.

SUMMARY OF THE INVENTION

It is an object of this invention to provide an improved apparatus for detecting a condition of burning in an internal combustion engine.

A first aspect of this invention provides an apparatus for detecting a condition of burning which comprises a pair of opposed electrodes provided in a combustion chamber of an internal combustion engine; AC voltage applying means for applying an AC voltage between the opposed electrodes; current detecting means for detecting a current flowing between the opposed electrodes, and for outputting a current-representing signal depending on the detected current; and burning ion current extracting means for removing a capacitive current component from the current-representing signal to extract a burning ion current component, the capacitive current component occurring in correspondence with the AC voltage, the burning ion current component corresponding to a burning ion current which flows between the opposed electrodes.

A second aspect of this invention is based on the first aspect thereof, and provides an apparatus wherein the burning ion current extracting means comprises detected current controlling means for implementing control so as to output the current-representing signal at a given phase with respect to the AC voltage.

A third aspect of this invention is based on the second aspect thereof, and provides an apparatus wherein the detected current controlling means comprises a voltage trigger generating circuit for generating a trigger at a given phase with respect to the AC voltage, and a sample-and-hold circuit for latching the current-representing signal when the trigger is generated, the sample-and-hold circuit outputting a burning-ion-current representing signal.

A fourth aspect of this invention is based on the first aspect thereof, and provides an apparatus wherein the burning ion current extracting means comprises phase difference detecting means for detecting a phase difference between the AC voltage and the current-representing signal, and for outputting a burning-ion-current representing signal in response to the detected phase difference.

A fifth aspect of this invention is based on the fourth aspect thereof, and provides an apparatus wherein the phase difference detecting means comprises a first phase trigger generating circuit for generating a first trigger at a given phase with respect to the AC voltage, a second phase trigger generating circuit for generating a second trigger when the current-representing signal reaches a given level, and a time measuring circuit for measuring a time from a moment of occurrence of the first trigger to a moment of occurrence of the second trigger, the measured time being the detected phase difference.

A sixth aspect of this invention is based on the first aspect thereof, and provides an apparatus wherein the burning ion current extracting means comprises capacitive current generating means for generating a capacitive-current representing signal having a given phase with respect to the AC voltage, and a subtracting circuit for generating a burning-ion-current generating signal corresponding to a difference between the capacitive-current representing signal and the current representing signal.

A seventh aspect of this invention is based on the sixth aspect thereof, and provides an apparatus wherein the capacitive current generating means comprises a differentiating circuit for differentiating the AC voltage into the capacitive-current representing signal.

An eighth aspect of this invention is based on the sixth aspect thereof, and provides an apparatus further comprising calculating means for calculating a ratio between a parameter represented by the burning-ion-current representing signal and a parameter represented by a signal depending on the AC voltage applied between the opposed electrodes.

A ninth aspect of this invention is based on the seventh aspect thereof, and provides an apparatus further comprising calculating means for calculating a ratio between a parameter represented by the burning-ion-current representing signal and a parameter represented by a signal depending on the AC voltage applied between the opposed electrodes.

A tenth aspect of this invention provides an apparatus for detecting a condition of burning in an internal combustion engine, comprising a pair of opposed electrodes provided in a combustion chamber of the engine; AC voltage applying means for applying an AC voltage between the opposed electrodes; current detecting means for detecting a current flowing between the opposed electrodes, and for generating a current-representing signal depending on the detected current; waveform processing means for removing a capacitive current component from the current-representing signal to extract a burning ion current component, and for generating a burning-ion-current representing signal depending on the extracted burning ion current component, the capacitive current component occurring in correspondence with the AC voltage, the burning ion current component corresponding to a burning ion current which flows between the opposed electrodes;

and burning condition detecting means for detecting a condition of burning in the combustion chamber of the engine on the basis of the burning-ion-current representing signal generated by the waveform processing means; wherein the waveform processing means comprises integration processing means for integrating the current-representing signal to generate the burning-ion-current representing signal.

An eleventh aspect of this invention is based on the tenth aspect thereof, and provides an apparatus wherein the integration processing means comprises a low pass filter.

A twelfth aspect of this invention is based on the tenth aspect thereof, and provides an apparatus wherein the burning condition detecting means comprises an integrator for integrating the burning-ion-current representing signal generated by the waveform processing means during a predetermined interval, and means for deciding that the combustion chamber of the engine is in a misfire state when a value of a result of the integrating by the integrator is lower than a predetermined reference value.

A thirteenth aspect of this invention is based on the tenth aspect thereof, and provides an apparatus wherein the burning condition detecting means comprises peak value detecting means for detecting a peak value of the burning-ion-current representing signal generated by the waveform processing means, and means for deciding that the combustion chamber of the engine is in a misfire state when the peak value detected by the peak value detecting means is lower than a predetermined reference value.

A fourteenth aspect of this invention is based on the tenth aspect thereof, and provides an apparatus wherein the burning condition detecting means comprises knock component extracting means for extracting a knock-related component from the burning-ion-current representing signal generated by the waveform processing means, the knock-related component has a predetermined frequency corresponding to a knocking; maximum amplitude detecting means for detecting a maximum value of an amplitude of the knock-related component extracted by the knock component extracting means; and means for deciding that the combustion chamber of the engine is in a knocking state when the maximum value detected by the maximum amplitude detecting means is equal to or greater than a predetermined reference value.

A fifteenth aspect of this invention is based on the tenth aspect thereof, and provides an apparatus wherein the burning condition detecting means comprises knock component extracting means for extracting a knock-related component from the burning-ion-current representing signal generated by the waveform processing means, the knock-related component has a predetermined frequency corresponding to a knocking; a half-wave rectifier for half-wave-rectifying the knock-related component extracted by the knock component extracting means during a predetermined interval: an integrator for integrating an output signal of the half-wave rectifier; and means for deciding that the combustion chamber of the engine is in a knocking state when a value of a result of the integrating by the integrator is equal to or greater than a predetermined reference value.

A sixteenth aspect of this invention is based on the fourteenth aspect thereof, and provides an apparatus wherein the knock component extracting means comprises a high pass filter.

A seventeenth aspect of this invention is based on the fifteenth aspect thereof, and provides an apparatus wherein the knock component extracting means comprises a high pass filter.

BRIEF DESCRIPTION OF THE DRAWINGS

FIG. 7 is a time-domain diagram of various signals in the apparatus of FIG. 6.

DESCRIPTION OF THE PREFERRED EMBODIMENTS

First Embodiment

Figure 1:
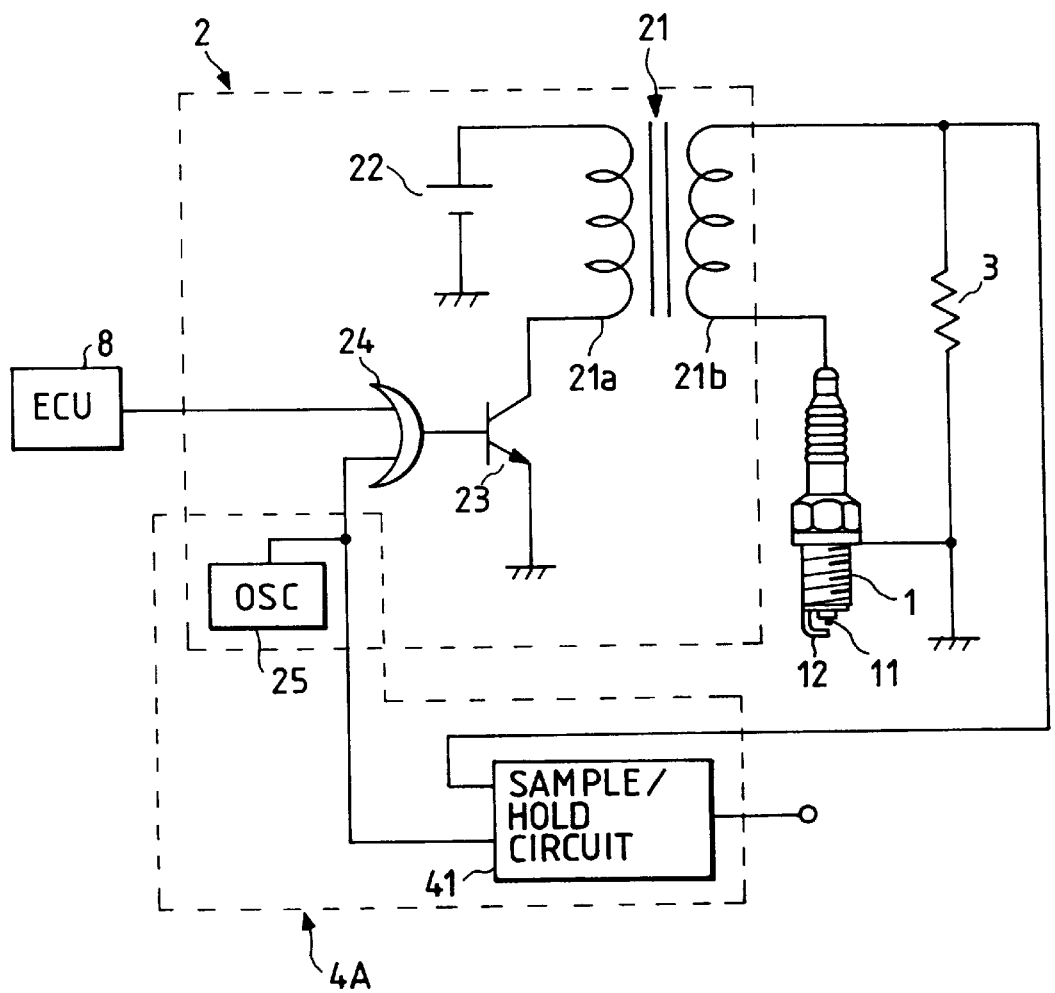
FIG. 1 is a diagram of an apparatus for detecting a condition of burning in an internal combustion engine according to a first embodiment of this invention.

With reference to FIG. 1, an apparatus for detecting a condition of burning in an internal combustion engine includes a spark plug 1 provided in a combustion chamber of the engine. The spark plug 1 has a pair of opposed electrodes 11 and 12. One end of a secondary winding 21b of a transformer 21 is connected to the opposed electrode 11 of the spark plug 1. The transformer 21 is contained in an AC voltage applying device (an AC voltage applying means) 2.

In the AC voltage applying device 2, one end of a primary winding 21a of the transformer 21 is connected to the positive terminal of a battery 22. The negative terminal of the battery 22 is grounded. The other end of the primary winding 21a of the transformer 21 is connected to the collector of an NPN switching transistor 23. The emitter of the switching transistor 23 is grounded. The switching transistor 23 serves to selectively make on and off the voltage applied from the battery 22. The. AC voltage applying device 2 also includes an oscillator 25 generating and outputting a rectangular wave signal having a frequency of, for example, 20 kHz or 30 kHz. The rectangular wave signal is fed to the base of the switching transistor 23 from the oscillator 25 via an OR gate 24 having two input terminals.

A fixed resistor 3 is connected between the other end of the secondary winding 21b of the transformer 21 and the opposed electrode 12 of the spark plug 1. The fixed resistor 3 is a sensing resistor which serves as a current sensing device (a current sensing means) for detecting a current flowing between the opposed electrodes 11 and 12 of the spark plug 1. Specifically, the voltage across the sensing resistor 3 represents the current flowing between the opposed electrodes 11 and 12 of the spark plug 1. The opposed electrode 12 of the spark plug 1 is grounded. The junction between the sensing resistor 3 and the secondary winding 21b of the transformer 21 is connected to the input terminal of a sample-and-hold circuit 41 so that the voltage across the sensing resistor 3 is applied to the sample-and-hold circuit 41. The sample-and-hold circuit 41 is contained in a detected current controlling device (a detected current controlling means) 4A being a burning ion current extracting device (a burning ion current extracting means).

The oscillator 25 also serves as a voltage trigger generating circuit contained in the detected current controlling device 4A.

The rectangular wave signal is inputted from the oscillator 25 into the sample-and-hold circuit 41 as a sampling clock signal or a sample timing signal. Every change of the rectangular wave signal from an H level to an L level is a trigger which enables the sample-and-hold circuit 41 to latch the voltage fed from the sensing resistor 3.

The spark plug 1 and a portion of the AC voltage applying device 2 cooperate to ignite an air-fuel mixture in the combustion chamber of the engine. The transformer 21 serves as an ignition coil. An electronic control unit (ECU) 8 is connected to the base of the switching transistor 23 via the OR gate 24. The ECU 8 outputs a spark control signal to the base of the switching transistor 23 via the OR gate 24. When the ECU 8 outputs an H-level spark control signal to the base of the switching transistor 23 via the OR gate 24, the emitter-collector path of the switching transistor 23 is made on so that ignition energy is stored into the transformer 21 from the battery 22. When the spark control signal returns from the H level to an L level, electromagnetic induction in the transformer 21 generates a high voltage (a high tension) across the secondary winding 21b of the transformer 21. The generated high voltage is applied between the opposed electrodes 11 and 12 of the spark plug 1 so that a spark discharge occurs therebetween. The spark discharge ignites the air-fuel mixture.

Figure 2:
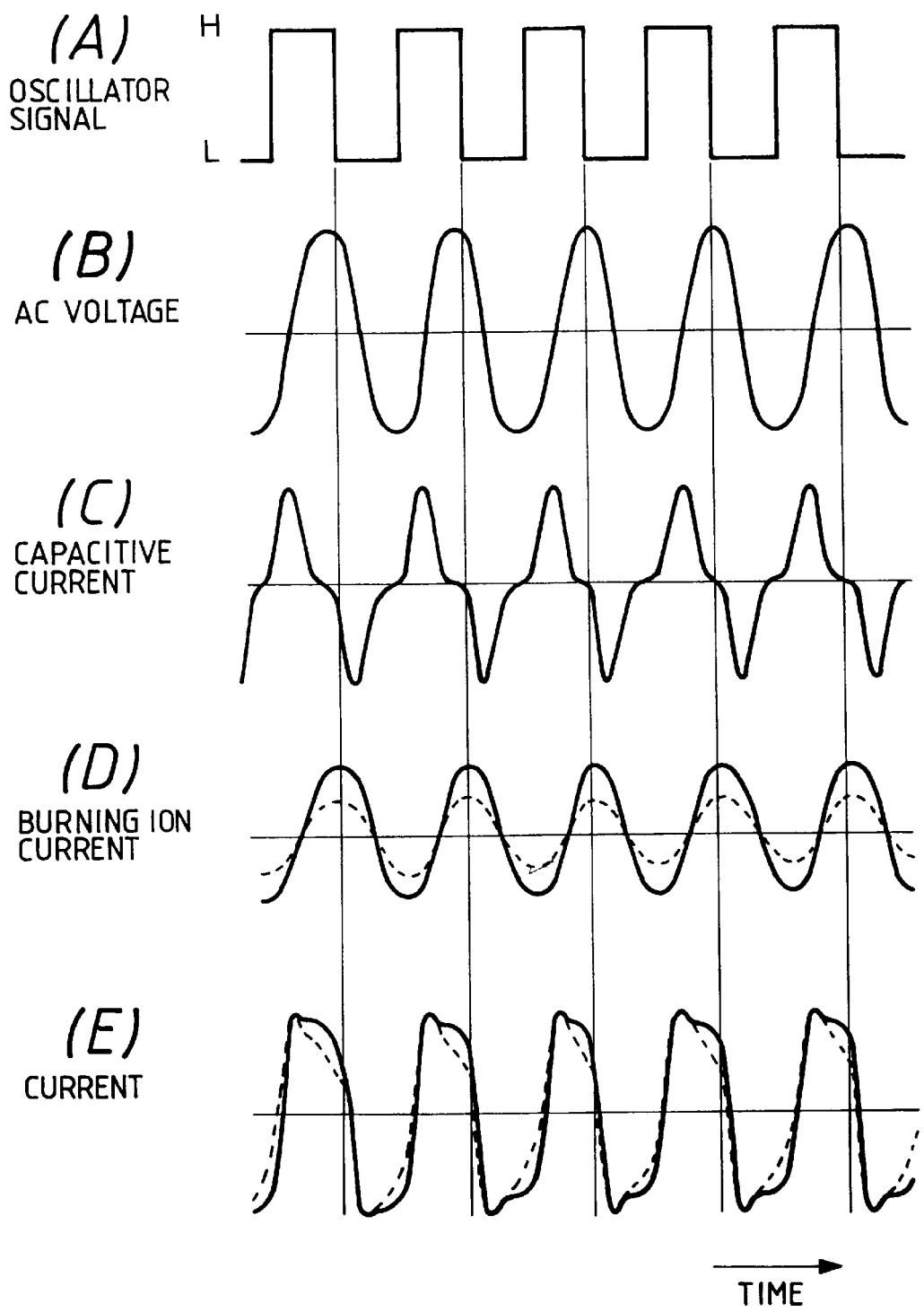
FIG. 2 is a time-domain diagram of various signals and parameters in the apparatus of FIG. 1.

Operation of the apparatus of FIG. 1 will be described with reference to FIG. 2. The rectangular wave signal fed from the oscillator 25 to the base of the switching transistor 23 via the OR gate 24 periodically changes between an H level and an L level as shown in the portion (A) of FIG. 2. The rectangular wave signal is also referred to as the oscillator signal. The emitter-collector path of the switching transistor 23 is periodically made conductive and non-conductive in response to the rectangular wave signal (the oscillator signal) so that the voltage applied from the battery 22 to the primary winding 21a of the transformer 21 is also periodically made on and off. Electromagnetic induction in the transformer 21 causes a high AC voltage across the secondary winding 21b of the transformer 21 in response to the periodical on/off voltage applied to the primary winding 21a thereof. The high AC voltage across the secondary winding 21b of the transformer 21 is applied between the opposed electrodes 11 and 12 of the spark plug 1. As shown in the portion (B) of FIG. 2, the high AC voltage applied between the opposed electrodes 11 and 12 of the spark plug 1 has a sinusoidal waveform due to the voltage smoothing effects of stray capacitances related to the switching transistor 23 and the transformer 21. The high AC voltage applied between the opposed electrodes 11 and 12 of the spark plug 1 has a frequency equal to the frequency of the rectangular wave signal generated by the oscillator 25. In addition, the high AC voltage applied between the opposed electrodes 11 and 12 of the spark plug 1 has a phase which retards from the phase of the rectangular wave signal (the oscillator signal) by about 90°.

A current is driven between the opposed electrodes 11 and 12 of the spark plug 1 by the high AC voltage applied therebetween. Under conditions where the air-fuel mixture ignites and bums, the actual current flowing between the opposed electrodes 11 and 12 of the spark plug 1 has a first component corresponding to a capacitive current, and a second component corresponding to a burning ion current. As shown in the portion (C) of FIG. 2, the capacitive current periodically alternates. The capacitive current is directly caused by the high AC voltage. The capacitive current is proportional to a differential of the high AC voltage with respect to time. Therefore, the amplitude of the capacitive current increases as the frequency of the high AC voltage rises. The amplitude of the capacitive current is independent of the amount or the density of ions caused by the burning. The capacitive current has a phase which is fixed relative to the phase of the high AC voltage independent of the amount or the density of ions caused by the burning. The capacitive current becomes null substantially at the moment of the occurrence of every change of the rectangular wave signal (the oscillator signal) from the H level to the L level. The burning ion current is caused by ions generated due to the burning. The burning ion current depends on the amount or the density of ions caused by the burning. The solid-line curve in the portion (D) of FIG. 2 denotes the burning ion current which occurs at a great amount or a high density of burning ions. The broken-line curve in the portion (D) of FIG. 2 denotes the burning ion current which occurs at a small amount or a low density of burning ions. The burning ion current alternates at a phase equal to the phase of the high AC voltage. The burning ion current has an amplitude which is proportional to the amount of burning ions, which form carriers, in a region between the opposed electrodes 11 and 12 of the spark plug 1. The burning ion current peaks substantially at the moment of the occurrence of every change of the rectangular wave signal (the oscillator signal) from the H level to the L level. The actual current flowing between the opposed electrodes 11 and 12 of the spark plug 1 is substantially equal to the resultant of the capacitive current and the burning ion current. The solid-line curve in the portion (E) of FIG. 2 denotes the actual current flowing between the opposed electrodes 11 and 12 of the spark plug 1 which occurs at a great amount or a high density of burning ions. The broken-line curve in the portion (E) of FIG. 2 denotes the actual current flowing between the opposed electrodes 11 and 12 of the spark plug 1 which occurs at a small amount or a low density of burning ions.

The actual current flowing between the opposed electrodes 11 and 12 of the spark plug 1 is detected by the sensing resistor 3. Specifically, the voltage across the sensing resistor 3 is proportional to the actual current flowing between the opposed electrodes 11 and 12 of the spark plug 1. The voltage across the sensing resistor 3 is fed to the sample-and-hold circuit 41 as a signal (a current-representing signal) representing the actual current flowing between the opposed electrodes 11 and 12 of the spark plug 1.

Each time the high AC voltage peaks, the rectangular wave signal (the oscillator signal) changes from the H level to the L level. The sample-and-hold circuit 41 latches (samples and holds) the current-representing signal at a timing equal to the moment of the occurrence of every change of the rectangular wave signal from the H level to the L level. The sample-and-hold circuit 41 outputs the latched current-representing signal as a signal indicating the burning ion current. When the rectangular wave signal (the oscillator signal) changes from the H level to the L level, the capacitive current becomes null and hence absent from the actual current flowing between the opposed electrodes 11 and 12 of the spark plug 1. In addition, when the rectangular wave signal (the oscillator signal) changes from the H level to the L level, the burning ion current peaks. Accordingly, the latching process by the sample-and-hold circuit 41 provides accurate and efficient detection of the burning ion current. In the case where the frequency of the rectangular wave signal generated by the oscillator 25 is equal to 30 kHz, a temporal sequence (a temporal train) of 30 samples of the burning ion current signal is available per 1 msec. Thus, the number (the amount) or the density of burning ions is periodically detected during every burning cycle related to the operation of the engine.

This embodiment may be modified as follows. A first modification of this embodiment uses an exclusive ion probe in place of the spark plug. The exclusive ion probe has a pair of opposed electrodes. According to a second modification of this embodiment, the sample-and-hold circuit 41 latches (samples and holds) the current-representing signal at a timing equal to the moment of the occurrence of every change of the rectangular wave signal (the oscillator signal) from the L level to the H level. It should be noted that the burning ion current also peaks substantially at the moment of the occurrence of every change of the rectangular wave signal (the oscillator signal) from the L level to the H level. According to a third modification of this embodiment, the sample-and-hold circuit 41 latches (samples and holds) the current-representing signal at another timing. A fourth modification of this embodiment uses a coil or an inductor in place of the sensing resistor 3. The coil or the inductor constitutes a current sensing device (a current sensing means).

Second Embodiment

An apparatus for detecting a condition of burning in an internal combustion engine according to a second embodiment of this invention includes a spark plug, an AC voltage applying device (an AC voltage applying means), and a sensing resistor similar to the spark plug 1, the AC voltage applying device 2, and the sensing resistor 3 in the apparatus of FIG. 1 respectively. The apparatus according to the second embodiment includes a burning ion current extracting device (a burning ion current extracting means) different from the burning ion current extracting device (the burning ion current extracting means) in the apparatus of FIG. 1. The apparatus according to the second embodiment includes a phase difference detecting device (a phase difference detecting means) being the burning ion current extracting device (the burning ion current extracting means).

Figure 3:
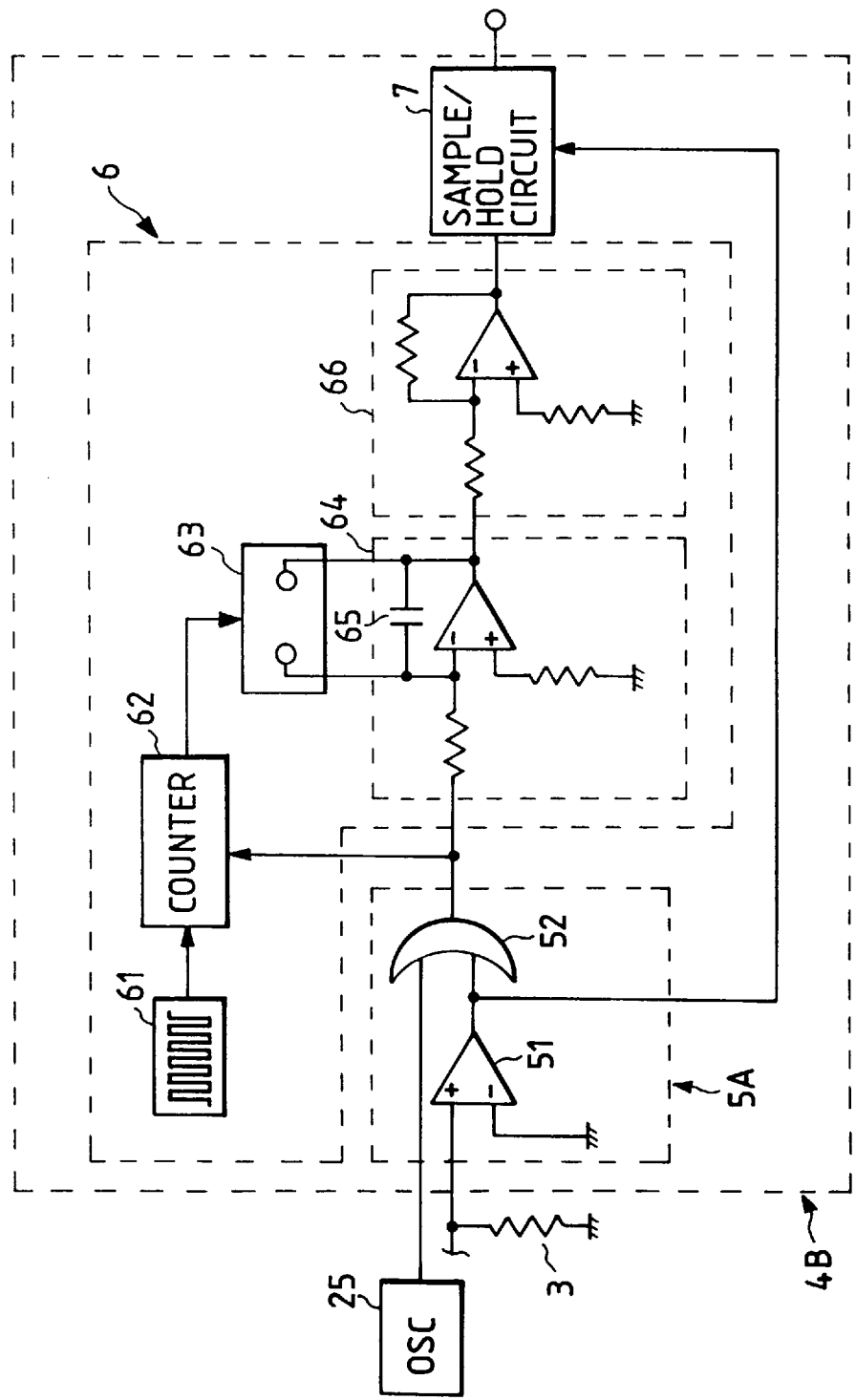
FIG. 3 is a diagram of a major portion of an apparatus for detecting a condition of burning in an internal combustion engine according to a second embodiment of this invention.

With reference to FIG. 3, the phase difference detecting device (the phase difference detecting means) includes an oscillator 25 and a phase difference measuring circuit 4B. The oscillator 25 serves as a phase trigger generating circuit. The phase difference measuring circuit 4B includes a trigger signal forming circuit 5A, a time measuring circuit 6, and a sample-and-hold circuit 7.

The trigger signal forming circuit 5A includes an OR gate 52 having two input terminals. The oscillator 25 outputs a rectangular wave signal to one of the input terminals of the OR gate 52. The rectangular wave signal outputted from the oscillator 25 has a given frequency equal to, for example, 20 kHz or 30 kHz . Every change of the rectangular wave signal (the oscillator signal) from an L level to an H level provides a first phase trigger. The trigger signal forming circuit 5A includes a comparator 51 which serves to generate a second phase trigger. A current-representing signal developed across a sensing resistor 3 is applied to a non-inventing input terminal of the comparator 51. An inverting input terminal of the comparator 51 is grounded. When the current-representing signal is positive, the comparator 51 outputs an H-level signal. Otherwise, the comparator 51 outputs an L-level signal. Every change of the output signal of the comparator 51 from the H level to the L level provides a second phase trigger. The output signal of the comparator 51 is applied to the other input terminal of the OR gate 52. During the time interval from the moment of the occurrence of a first phase trigger to the moment of the occurrence of a second phase trigger, the output signal of the OR gate 52 remains in an H-level state. The output signal of the OR gate 52 constitutes a trigger signal.

The time measuring circuit 6 includes an integrating circuit 64 which receives the output signal of the OR gate 52. The integrating circuit 64 serves to integrate the H-level signal outputted from the OR gate 52. The integrating circuit 64 includes a capacitor 65 connected to an analog switch 63. The analog switch 63 serves to selectively reset the integrating circuit 64.

The time measuring circuit 6 also includes an oscillator 61 and a counter 62. The oscillator 61 outputs a rectangular wave signal to the counter 62. The rectangular wave signal outputted from the oscillator 61 has a given frequency sufficiently higher than the frequency of the rectangular wave signal generated by the oscillator 25. The frequency of the rectangular wave signal outputted from the oscillator 61 is equal to, for example, 300 kHz. The device 62 counts pulses in the rectangular wave signal outputted from the oscillator 61. The counter 62 serves as a frequency divider operating on the rectangular wave signal outputted from the oscillator 61. The counter 62 outputs one pulse to the analog switch 63 per three pulses in the rectangular wave signal outputted from the oscillator 61. Every pulse outputted from the counter 62 to the analog switch 63 is a reset pulse which enables the analog switch 63 to reset the integrating circuit 64. The counter 62 is selectively enabled and disabled by the output signal of the OR gate 52. Only when the output signal of the OR gate 52 is in the L-level state, the counter 62 is enabled to count input pulses and to output a reset pulse.

The time measuring circuit 6 further includes an inverting circuit 66 which receives the output signal of the integrating circuit 64. The output signal of the integrating circuit 64 is negative. The inverting circuit 66 serves to invert the negative output signal of the integrating circuit 64 into a corresponding positive signal. The output signal of the inverting circuit 66 is applied to the sample-and-hold circuit 7.

The output signal of the comparator 51 is applied to the sample-and-hold circuit 7 as a sampling clock signal or a sample timing signal. Every change of the output signal of the comparator 51 from an H level to an L level is a trigger which enables the sample-and-hold circuit 7 to latch the output signal of the inverting circuit 66.

Figure 4:
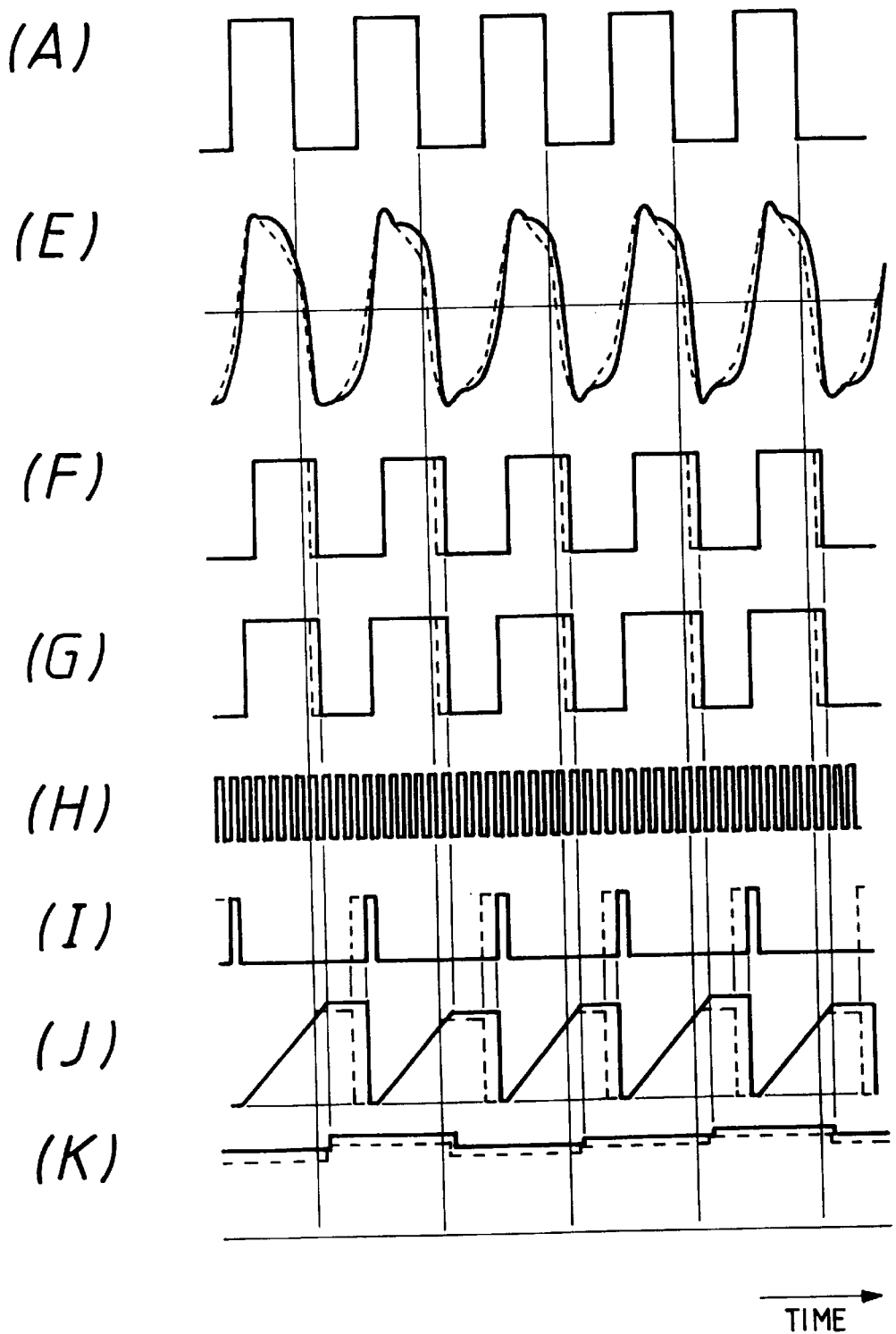
FIG. 4 is a time-domain diagram of various signals in the apparatus of FIG. 3.
Figure 5:
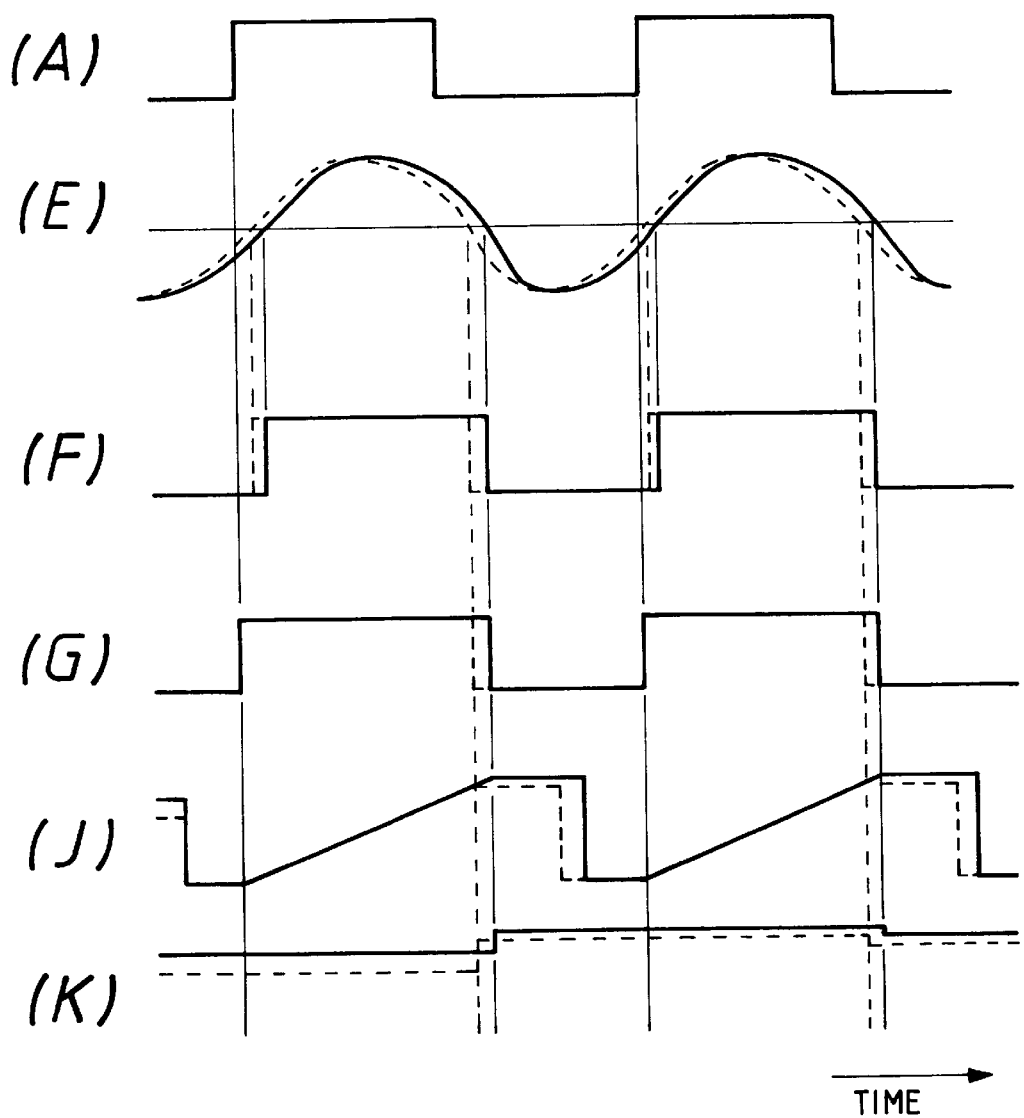
FIG. 5 is a time-domain diagram of various signals in the apparatus of FIG. 3.

Operation of the apparatus of FIG. 3 will be described with reference to FIGS. 4 and 5. In FIGS. 4 and 5, the solid-line curves denote conditions occurring at a great burning ion current while the broken-line curves denote conditions occurring at a small burning ion current. The rectangular wave signal outputted from the oscillator 25 periodically changes between an H level and an L level as shown in the portion (A) of FIG. 4 and the portion (A) of FIG. 5. Since the phase of the rectangular wave signal outputted from the oscillator 25, the phase of a high AC voltage across a secondary winding of a transformer 21 (FIG. 1), and the phase of a capacitive current are always constant as in the embodiment of FIGS. 1 and 2, every first phase trigger (every change of the rectangular wave signal from the L level to the H level) has a fixed phase relation with the high AC voltage applied between the opposed electrodes of a spark plug 1 (see FIG. 1).

The current-representing signal developed across the sensing resistor 3 alternates as shown in the portion (E) of FIG. 4 and the portion (E) of FIG. 5. The current-representing signal has a frequency equal to the frequency of the rectangular wave signal outputted from the oscillator 25. The output signal of the comparator 51 periodically changes between an H level and an L level as shown in the portion (F) of FIG. 4 and the portion (F) of FIG. 5. The output signal of the comparator 51 has a frequency equal to the frequency of the rectangular wave signal outputted from the oscillator 25. The comparator 51 outputs a H-level signal only when the voltage of the current-representing signal is higher than the ground potential. Accordingly, the comparator 51 outputs a second phase trigger when the current-representing signal changes from a positive state to a negative state or when the voltage of the current-representing signal falls to "0". Since a burning ion current peaks when the rectangular wave signal outputted from the oscillator 25 changes from the H level to the L level as previously described in connection with the embodiment of FIGS. 1 and 2, a timing (a phase) at which the current-representing signal developed across the sensing resistor 3 changes from a positive state to a negative state retards as the burning ion current increases. Therefore, the timing (the phase) of the outputting of a second phase trigger from the comparator 51 retards as the burning ion current increases.

The OR gate 52 outputs a trigger signal which results from logic OR operation between the output signal (the rectangular wave signal) of the oscillator 25 and the output signal of the comparator 51. The trigger signal periodically changes between an H level and an L level as shown in the portion (G) of FIG. 4 and the portion (G) of FIG. 5. The trigger signal has a frequency equal to the frequency of the rectangular wave signal outputted from the oscillator 25. The timing of the occurrence of every change of the trigger signal from the L level to the H level is equal to the timing of the occurrence of a corresponding first phase trigger. The timing of the occurrence of every change of the trigger signal from the H level to the L level is equal to the timing of the occurrence of a corresponding second phase trigger.

The output signal of the oscillator 61 periodically changes between an H level and an L level as shown in the portion (H) of FIG. 4. The output signal of the oscillator 61 has a frequency sufficiently higher than the frequency of the output signal of the oscillator 25. The output signal of the counter 62 has a train of pulses (reset pulses) as shown in the portion (I) of FIG. 4. During every time interval for which the output signal (the trigger signal) of the OR gate 52 remains in the L-level state, the counter 62 outputs one reset pulse to the analog switch 63 per three pulses in the output signal of the oscillator 61 so that the analog switch 63 resets the integrating circuit 64 in response to the reset pulse. The integrating circuit 64 starts to integrate the trigger signal each time the trigger signal changes to the H level. The output signal of the integrating circuit 64 is converted into a corresponding positive signal by the inverting circuit 66.

The output signal of the inverting circuit 66 periodically changes as shown in the portion (J) of FIG. 4 and the portion (J) of FIG. 5. During every time interval for which the trigger signal remains in the H-level state, the voltage of the output signal of the inverting circuit 66 continues to increase at a constant slope. During a former part of every time interval for which the trigger signal remains in the L-level state, the voltage of the output signal of the inverting circuit 66 continues to be equal to the voltage occurring at the end of the last H-level time interval related to the trigger signal. Since the voltage of the output signal of the inverting circuit 66 represents the value of the integration of the trigger signal, the voltage of the output signal of the inverting circuit 66 which occurs at the end of every H-level time interval related to the trigger signal is proportional to the length of the H-level time interval of the trigger signal.

The output signal of the inverting circuit 66 is fed to the sample-and-hold circuit 7. The output signal of the comparator 51 is applied to the sample-and-hold circuit 7 as a sampling clock signal or a sample timing signal. Each time the output signal of the comparator 51 changes from the H level to the L level (see the portion (F) of FIG. 4 and the portion (F) of FIG. 5), the sample-and-hold circuit 7 latches (samples and holds) the output signal of the inverting circuit 66. The sample-and-hold circuit 7 outputs the latched signal as a signal indicating the burning ion current. Since the timing of every change of the output signal of the comparator 51 from the H level to the L level is equal to the timing of the end of a corresponding H-level time interval related to the trigger signal, the voltage of the burning-ion-current indicating signal is proportional to the length of the H-level time interval of the trigger signal. The first phase triggers have a fixed phase relation with the capacitive current. Therefore, the length of every H-level time interval of the trigger signal is independent of the capacitive current. The output signal of the sample-and-hold circuit 7 is hence independent of the capacitive current, accurately representing the burning ion current. The output signal of the sample-and-hold circuit 7 periodically changes as shown in the portion (K) of FIG. 4 and the portion (K) of FIG. 5. The voltage of the output signal of the sample-and-hold circuit 7, which represents the burning ion current, is periodically updated for every period of the rectangular wave signal (the output signal of the oscillator 25).

It should be noted that the inverting input terminal of the comparator 51 may be subjected to a given voltage rather than the ground potential. In this case, a second phase trigger occurs each time the voltage of the current-representing signal reaches the given voltage.

Third Embodiment

Figure 6:
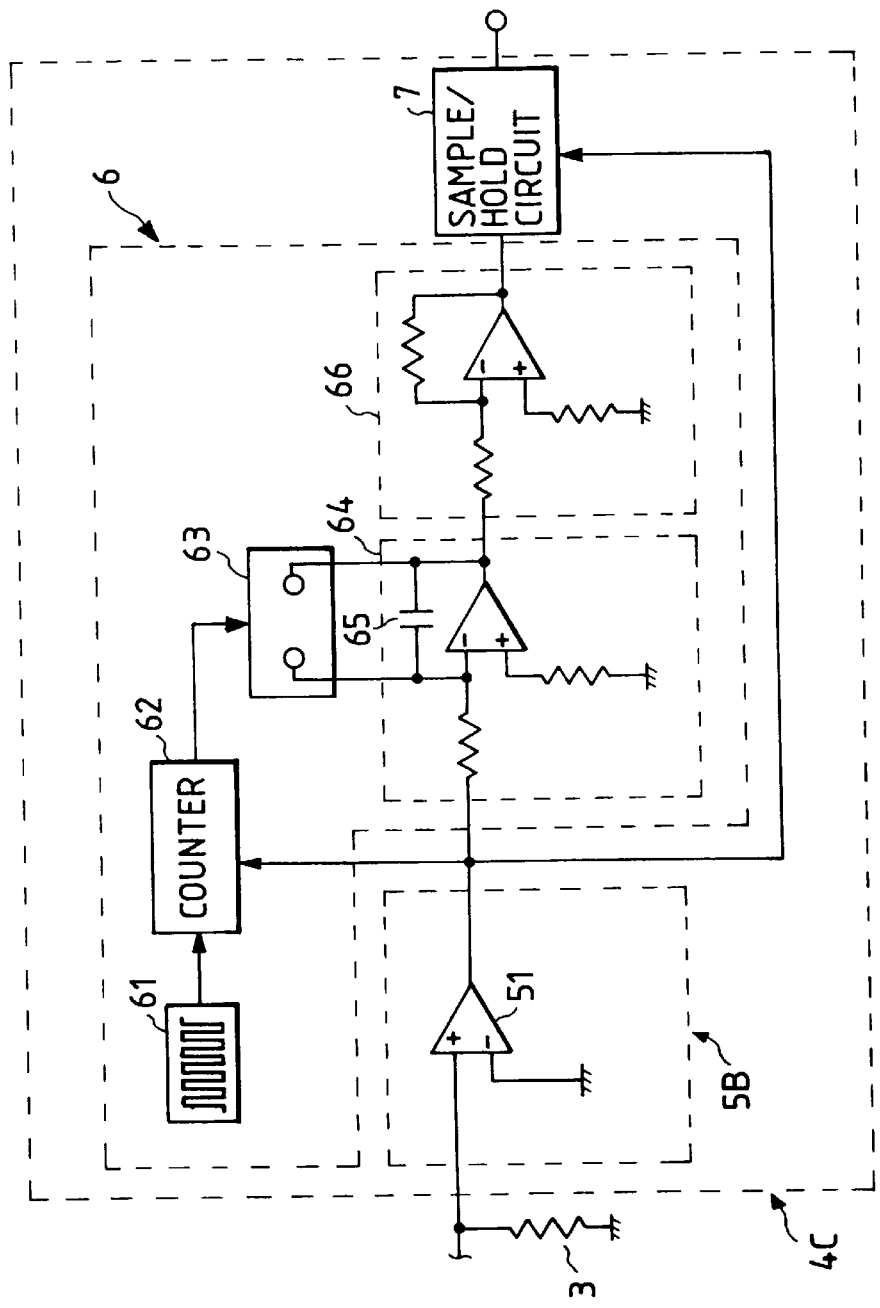
FIG. 6 is a diagram of a major portion of an apparatus for detecting a condition of burning in an internal combustion engine according to a third embodiment of this invention.

FIG. 6 shows an apparatus for detecting a condition of burning in an internal combustion engine according to a third embodiment of this invention. The apparatus of FIG. 6 is similar to the apparatus of FIG. 3 except that a phase difference measuring circuit 4C replaces the phase difference measuring circuit 4B (see FIG. 3). The phase difference measuring circuit 4C includes a trigger signal forming circuit 5B instead of the trigger signal forming circuit 5A (see FIG. 3). In other points, the phase difference measuring circuit 4C is similar to the phase difference measuring circuit 4B (see FIG. 3).

As shown in FIG. 6, the trigger signal forming circuit 5B includes a comparator 51 which serves to generate both a first phase trigger and a second phase trigger. A current-representing signal developed across a sensing resistor 3 is applied to a non-inventing input terminal of the comparator 51. An inverting input terminal of the comparator 51 is grounded. When the current-representing signal is positive, the comparator 51 outputs an H-level signal. Otherwise, the comparator 51 outputs an L-level signal. The output signal of the comparator 51 constitutes a trigger signal having a rectangular waveform. The output signal of the comparator 51 is inputted into an integrating circuit 64 and a counter 62. Every change of the trigger signal (the output signal of the comparator 51) from an L level to an H level provides a first phase trigger. Every change of the trigger signal (the output signal of the comparator 51) from the H level to the L level provides a second phase trigger. During every time interval for which the output signal of the comparator 51 remains in the L-level state, a counter 62 outputs one reset pulse to an analog switch 63 in response to three pulses in the output signal of an oscillator 61.

Operation of the apparatus of FIG. 6 will be described with reference to FIG. 7. In FIG. 7, the solid-line curves denote conditions occurring at a great burning ion current while the broken-line curves denote conditions occurring at a small burning ion current.

It is known that a burning ion current flowing between opposed electrodes of a spark plug tends to depend on the direction (the polarity) of a voltage applied therebetween. A possible cause of this fact is that burning ions have positive ions more than negative ions. The portion (D) of FIG. 7 shows examples of time-domain variations in a burning ion current. As shown in the portion (D) of FIG. 7, the absolute values of negative peaks of the burning ion current are remarkably smaller than the absolute values of positive peaks thereof. The portion (E) of FIG. 7 shows examples of time-domain variations in the current-representing signal developed across the sensing resistor 3. The portion (F) of FIG. 7 shows examples of time-domain variations in the output signal of the comparator 51. Since the burning ion current has very smaller values in a negative side than those in a positive side, the current-representing signal which occurs at its waveform rising part is substantially in good correspondence with a capacitive current. Accordingly, the timing of every change of the trigger signal (the output signal of the comparator 51) from the L level to the H level has a substantially fixed phase relation with a high AC voltage applied between the opposed electrodes of the spark plug. The timing of every change of the trigger signal (the output signal of the comparator 51) from the H level to the L level advances and retards in accordance with the ion burning current. Accordingly, the length of every H-level time interval related to the trigger signal is independent of the capacitive current, accurately representing the burning ion current.

The apparatus of FIG. 6 is simpler than the apparatus of FIG. 3 in that the OR gate 52 (see FIG. 3) is omitted therefrom.

It should be noted that the inverting input terminal of the comparator 51 may be subjected to a given voltage rather than the ground potential. In this case, a second phase trigger occurs each time the voltage of the current-representing signal reaches the given voltage.

Fourth Embodiment

Figure 8:
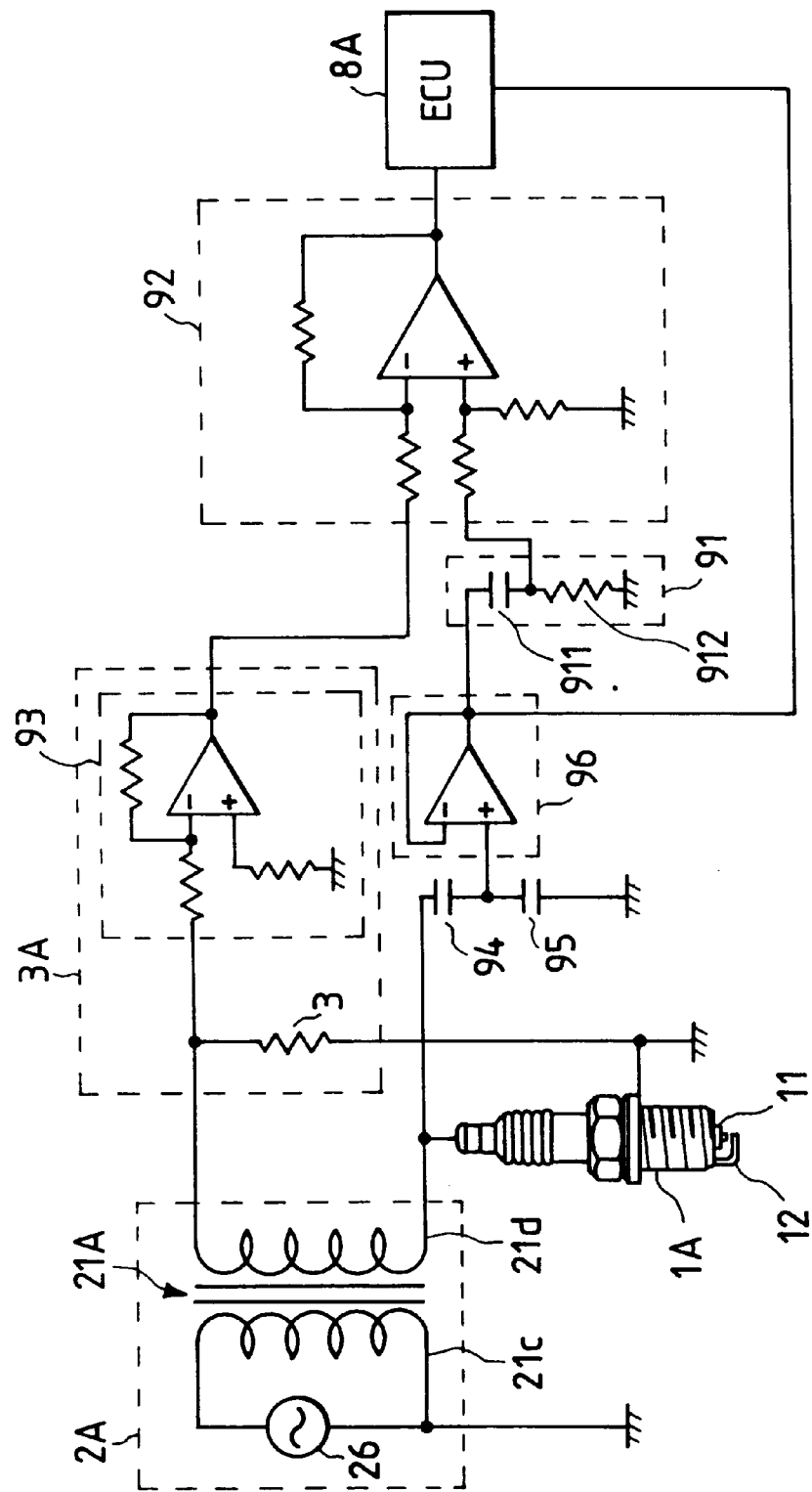
FIG. 8 is a diagram of an apparatus for detecting a condition of burning in an internal combustion engine according to a fourth embodiment of this invention.

With reference to FIG. 8, an apparatus for detecting a condition of burning in an internal combustion engine includes an ion probe 1A provided in a combustion chamber of the engine. The ion probe 1A is similar in structure to the spark plug 1 of FIG. 1. The ion probe 1A has a pair of opposed electrodes 11 and 12. One end of a secondary winding 21d of a transformer 21A is connected to the opposed electrode 11 of the ion probe 1A. The transformer 21A is contained in an AC voltage applying device (an AC voltage applying means) 2A. The opposed electrode 12 of the ion probe 1A is grounded. In the AC voltage applying device 2A, an AC power supply 26 is connected to a primary winding 21c of the transformer 21A.

A fixed resistor 3 is connected between the other end of the secondary winding 21d of the transformer 21A and the opposed electrode 12 of the ion probe 1A. The fixed resistor 3 is a sensing resistor contained in a current sensing device (a current sensing means) 3A for detecting a current flowing between the opposed electrodes 11 and 12 of the ion probe 1A. Specifically, the voltage across the sensing resistor 3 is proportional to the current flowing between the opposed electrodes 11 and 12 of the ion probe 1A. The voltage across the sensing resistor 3 is inputted into an inverting amplifier circuit 93. The inverting amplifier circuit 93 inverts the input voltage into a current-representing signal which is positive when the current flows from the opposed electrode 11 to the opposed electrode 12 of the ion probe 1A. The current-representing signal is fed from the inverting amplifier circuit 93 to an inverting input terminal of a subtracting circuit 92.

A first end of a capacitor 94 is connected to the opposed electrode 11 of the ion probe 1A. A second end of the capacitor 94 is connected to a first end of a capacitor 95. A second end of the capacitor 95 is grounded. Accordingly, the series combination of the capacitors 94 and 95 is connected between the opposed electrodes 11 and 12 of the ion probe 1A. The combination of the capacitors 94 and 95 divides a voltage applied between the opposed electrodes 11 and 12 of the ion probe 1A. The voltage across the capacitor 95 which results from the division of the voltage applied between the opposed electrodes 1 1 and 12 of the ion probe 1A is fed via a buffer amplifier 96 to an electronic control unit (ECU) 8A as a voltage-representing signal. The ECU 8A serves as a calculating device (a calculating means). The output signal of the buffer amplifier 96 is inputted into a differentiating circuit 91. The differentiating circuit 91 includes a combination of a capacitor 911 and a resistor 912. The differentiating circuit 91 differentiates the output signal of the buffer amplifier 96 into a capacitive-current representing signal. The capacitive-current representing signal (the output signal of the differentiating circuit 91) is applied to a non-inverting input terminal of the subtracting circuit 92.

The subtracting circuit 92 includes a differential amplifier having two input terminals which receive the current-representing signal and the capacitive-current representing signal from the inverting amplifier circuit 93 and the differentiating circuit 91 respectively. The subtracting circuit 92 outputs a signal representing the difference between the current-representing signal and the capacitive-current representing signal. The output signal of the subtracting circuit 92 constitutes a burning-ion-current representing signal fed to the ECU 8A. The ECU 8A includes a combination of a microcomputer and A/D converters. The ECU 8A executes calculations responsive to the output signal of the buffer amplifier 96 and the output signal (the burning-ion-current representing signal) of the subtracting circuit 92.

Figure 9:
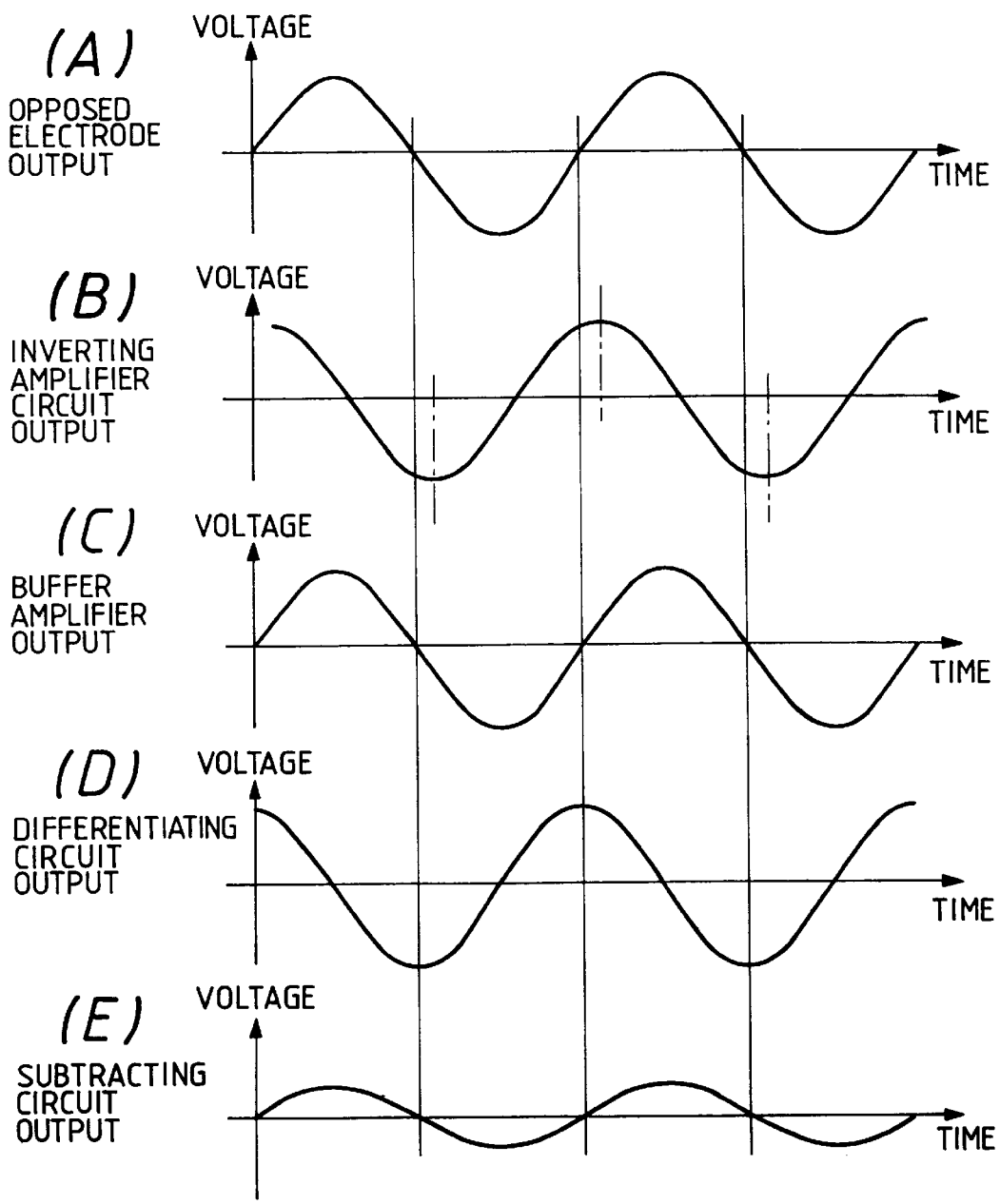
FIG. 9 is a time-domain diagram of various signals in the apparatus of FIG. 8.

Operation of the apparatus of FIG. 8 will be described with reference to FIG. 9. An AC signal outputted from the AC power supply 26 is boosted in voltage by the transformer 21A. The boost-resultant AC voltage generated by the transformer 21A is applied between the opposed electrodes 11 and 12 of the ion probe 1A. The portion (A) of FIG. 9 shows an example of a time-domain variation in the AC voltage applied between the opposed electrodes 11 and 12 of the ion probe 1A. The portion (B) of FIG. 9 shows an example of a time-domain variation in the current-representing signal (the output signal of the inverting amplifier circuit 93). Since a current flowing from the opposed electrode 11 to the opposed electrode 12 of the ion probe 1A is equal to a current flowing into the sensing resistor 3 from the ground side, the output signal of the inverting output circuit 93 has a sign (a polarity) which agrees with the sign (the polarity) of the current flowing from the opposed electrode 11 to the opposed electrode 12 of the ion probe 1A. The current flowing between the opposed electrodes 11 and 12 of the ion probe 1A has both a burning ion current and a capacitive current. Accordingly, the current flowing between the opposed electrodes 11 and 12 of the ion probe 1A is equivalent to an AC signal having a phase different from the phase of the AC voltage applied between the opposed electrodes 11 and 12 of the ion probe 1A.

The portion (C) of FIG. 9 shows an example of a time-domain variation in the output signal of the buffer amplifier 96. The output signal of the buffer amplifier 96 has a phase equal to the phase of the AC voltage applied between the opposed electrodes 11 and 12 of the ion probe 1A (see the portion (A) of FIG. 9). The portion (D) of FIG. 9 shows an example of a time-domain variation in the capacitive-current representing signal outputted from the differentiating circuit 91. The portion (E) of FIG. 9 shows an example of a time-domain variation in the burning-ion-current representing signal outputted from the subtracting circuit 92. The capacitive-current representing signal has a phase which advances from the phase of the output signal of the buffer amplifier 96 by 90°. Since the phase of the capacitive current advances, by 90°, from the phase of the AC voltage applied between the opposed electrodes 11 and 12 of the ion probe 1A, the capacitive-current representing signal is equal in sign (polarity) to the capacitive current. In addition, the voltage of the capacitive-current representing signal is proportional to the level (the magnitude) of the capacitive current. The parameters of the circuit elements and components in the apparatus of FIG. 8 are chosen so that the current representing signal fed to the subtracting circuit 92 from the inverting amplifier circuit 93 is equal in conversion factors to the capacitive-current representing signal fed to the subtracting circuit 92 from the differentiating circuit 91.

Accordingly, the burning-ion-current representing signal outputted from the subtracting circuit 92 corresponds to the result of subtracting the capacitive current from the current flowing between the opposed electrodes 11 and 12 of the ion probe 1A. Specifically, the voltage of the burning-ion-current representing signal is proportional to the level (the magnitude) of the burning ion current. The voltage of the burning ion-current representing signal is independent of the capacitive current.

The ECU 8A receives the output signal of the buffer amplifier 96 which is proportional to the AC voltage applied between the opposed electrodes 11 and 12 of the ion probe 1A. The ECU 8A receives the burning-ion-current representing signal from the subtracting circuit 92. The ECU 8A calculates a ratio "v/i" for every fixed control period sufficiently shorter than the frequency of the output signal of the AC power supply 26, where "v" denotes the parameter represented by the output signal of the buffer amplifier 96 and "i" denotes the parameter represented by the burning-ion-current representing signal. The calculated ratio "v/i" indicates a resistance which contributes to the burning ion current, and which depends on the density or the amount of burning ions present in a region between the opposed electrodes 11 and 12 of 20 the ion probe 1A. The instantaneous value of the resistance is available for every control period independent of the period of the AC voltage applied between the opposed electrodes 11 and 12 of the ion probe 1A. Therefore, it is possible to accurately detect a time-domain variation in the density or the amount of burnings ions.

Fifth Embodiment

Figure 10:
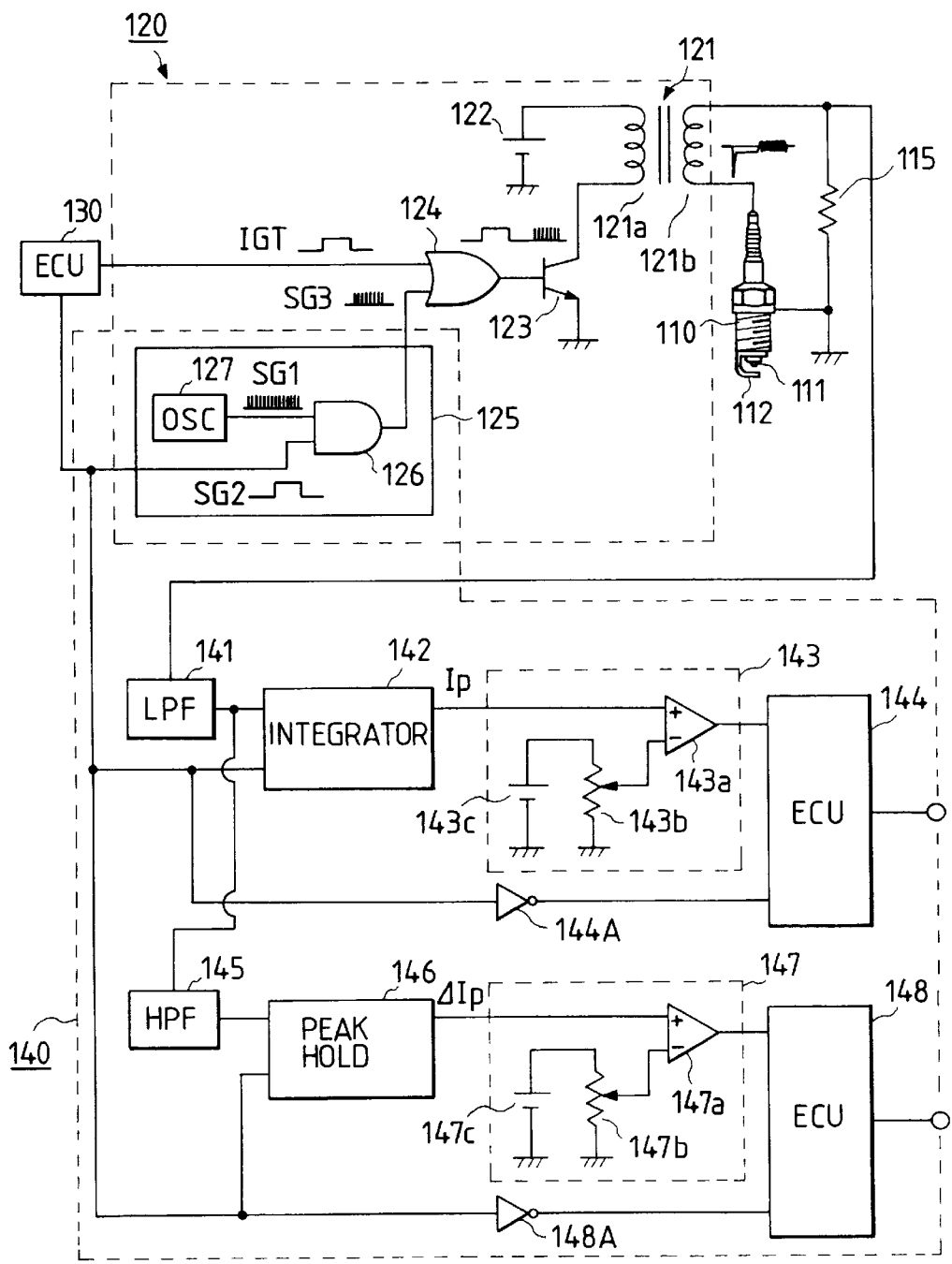
FIG. 10 is a diagram of an apparatus for detecting a condition of burning in an internal combustion engine according to a fifth embodiment of this invention.

With reference to FIG. 10, an apparatus for detecting a condition of burning in an internal combustion engine includes a spark plug 110 provided in a combustion chamber of the engine. The spark plug 110 has a pair of opposed electrodes 111 and 112. One end of a secondary winding 121b of a transformer 121 is connected to the opposed electrode 111 of the spark plug 110. The other end of the secondary winding 121b of the transformer 121 is connected to the opposed electrode 112 of the spark plug 110 via a fixed resistor 115. The transformer 121 is contained in a high-voltage applying circuit (an AC voltage applying means) 120.

In the high-voltage applying circuit 120, one end of a primary winding 121a of the transformer 121 is connected to the positive terminal of a battery 122. The negative terminal of the battery 122 is grounded. The other end of the primary winding 121a of the transformer 121 is connected to the collector of an NPN switching transistor 123. The emitter of the switching transistor 123 is grounded. The switching transistor 123 serves to selectively make on and off the voltage applied from the battery 122. The output terminal of an OR gate 124 is connected to the base of the switching transistor 123. The OR gate has 124 has first and second input terminals. The high-voltage applying circuit 120 also includes a signal generator 125 producing a rectangular wave signal having a frequency of, for example, 20 kHz. The signal generator 125 intermittently outputs the rectangular wave signal. The output terminal of the signal generator 125 is connected to the first input terminal of the OR gate 124. The rectangular wave signal is fed from the signal generator 125 to the base of the switching transistor 123 via the OR gate 124.

An electronic control unit (ECU) 130 is connected to the second input terminal of the OR gate 124. The ECU 130 includes, for example, a microcomputer or a similar device. The ECU 130 is used for control of the engine. The ECU 130 generates a spark control signal (an ignition control signal) IGT in response to operating conditions of the engine. The ECU 130 outputs the spark control signal IGT to the base of the switching transistor 123 via the OR gate 124.

The spark plug 110 and a portion of the high-voltage applying circuit 120 cooperate to ignite an air-fuel mixture in the combustion chamber of the engine. The transformer 121 serves as an ignition coil. When the ECU 130 outputs an H-level spark control signal IGT to the base of the switching transistor 123 via the OR gate 124, the emitter-collector path of the switching transistor 123 is made on so that ignition energy is stored into the transformer 121 from the battery 122. When the spark control signal IGT returns from the H level to an L level, electromagnetic induction in the transformer 121 generates a high voltage (a high tension) across the secondary winding 121b of the transformer 121. The generated high voltage is applied between the opposed electrodes 111 and 112 of the spark plug 110 so that a spark discharge occurs therebetween. The spark discharge ignites the air-fuel mixture.

The signal generator 125 includes an AND gate 126 and an oscillator 127. The output terminal of the AND gate 126 is connected to the first input terminal of the OR gate 124. The AND gate has first and second input terminals. The oscillator 127 generates and outputs a rectangular wave signal SG1 having a frequency of, for example, 20 kHz. The output terminal of the oscillator 127 is connected to the first input terminal of the AND gate 126. Thus, the rectangular wave signal SG1 is applied from the oscillator 127 to the first input terminal of the AND gate 126. The second input terminal of the AND gate 126 is connected to the ECU 130. The ECU 130 generates a gate control signal SG2. The gate control signal SG2 alternates between an H-level state and an L-level state according to a predetermined timing relation with the spark control signal IGT. The ECU 130 outputs the gate control signal SG2 to the second input terminal of the AND gate 126. When the gate control signal SG2 is in the H-level state, the AND gate 126 is open so that the rectangular wave signal SG1 is allowed to travel from the oscillator 127 to the OR gate 124. When the gate control signal SG2 is in the L-level state, the AND gate 126 is closed so that the rectangular wave signal SG1 is inhibited from travelling from the oscillator 127 to the OR gate 124. The resultant output signal SG3 of the AND gate 126 is fed via the OR gate 124 to the base of the switching transistor 123. The timing relation between the spark control signal IGT and the gate control signal SG2 is as follows. The gate control signal SG2 changes from the L level to the H level when a predetermined length of time has elapsed from the moment of every H-to-L change of the spark control signal IGT.

While the AND gate 126 remains opened by the gate control signal SG2, the rectangular wave signal SG1 continues to travel from the oscillator 127 to the base of the switching transistor 123. The switching transistor 123 periodically changes between an on state and an off state in response to the rectangular wave signal SG1 so that an alternating current having a frequency equal to the frequency of the rectangular wave signal SG1 flows through the primary winding 121a of the transformer 121. A high alternating voltage (high AC voltage) corresponding to the alternating current in the primary winding 121a is induced across the secondary winding 121b of the transformer 121. Therefore, in this case, the high alternating voltage which corresponds to the rectangular wave signal SG1 is applied between the opposed electrodes 111 and 112 of the spark plug 110. The gate control signal SG2 is designed so that the high alternating voltage remains applied to the spark plug 110 during a predetermined time interval (or a predetermined crank angle interval) after the generation of every spark discharge by the spark plug 110.

The fixed resistor 115 is connected between the other end of the secondary winding 121b of the transformer 121 and the opposed electrode 112 of the spark plug 110. The fixed resistor 115 serves as a sensing resistor for detecting a current flowing between the opposed electrodes 111 and 112 of the spark plug 110. Specifically, the voltage across the sensing resistor 115 represents the current flowing between the opposed electrodes 111 and 112 of the spark plug 110. During the burning of the air-fuel mixture in the combustion chamber of the engine, an ion current flows between the opposed electrodes 111 and 112 of the spark plug 110. Accordingly, in this case, the fixed resistor 115 serves as an ion-current detecting means. The opposed electrode 112 of the spark plug 110 is grounded. The junction between the sensing resistor 115 and the secondary winding 121b of the transformer 121 is connected to the input terminal of a low pass filter (LPF) 141 so that the voltage across the sensing resistor 115 is applied to the low pass filter 141. The voltage across the sensing resistor 115 is referred to as an ion-current signal. The low pass filter 141 is contained in an ion-current processing circuit 140.

It should be noted that the signal generator 125 is contained in the high-voltage applying circuit 120 and also the ion-current processing circuit 140.

The low pass filter 141 receives the ion-current signal from the fixed resistor 115. The low pass filter 141 serves as a waveform processing means operating on the ion-current signal. The low pass filter 141 removes high-frequency components from the ion-current signal. The high-frequency components removed by the low pass filter 141 have frequencies equal to, for example, 20 kHz or higher. Generally, such high-frequency components are caused by periodical changes in a capacitance between the opposed electrodes 111 and 112 of the spark plug 110 and also periodical changes in conditions of burning-induced ions in response to the applied-voltage changes. Accordingly, the resultant output signal of the low pass filter 141 varies in accordance with only low-frequency increases and decreases in the amount or the density of ions generated by the burning. The cutoff frequency of the low pass filter 141 is set to, for example, about 8 kHz . The cutoff frequency of the low pass filter 141 may be set to a value in the range of about 8 kHz to about 20 kHz.

In the ion-current processing circuit 140, the low pass filter 141 is followed by an integrator 142 and a high pass filter (HPF) 145. The integrator 142 includes, for example, a filter circuit of the Chebyshev type. The integrator 142 is connected to the ECU 130. The integrator 142 receives the gate control signal SG2 from the ECU 130. The integrator 142 is selectively enabled and disabled by the gate control signal SG2. Only during every given time interval (or every given crank angle interval) determined by the gate control signal SG2, the device 142 integrates the output signal of the low pass filter 141. The integrator 142 serves to measure the summation of the burning ion current which corresponds to the total amount of ions generated by the burning. The integrator 142 changes the output signal of the low pass filter 141 into a signal representing the integration result value Ip (that is, the value of the result of the integration of the burning ion current).

In the ion-current processing circuit 140, the integrator 142 is followed by a first output judgment circuit 143. The first output judgment circuit 143 includes a comparator 143a, a variable resistor 143b, and a battery 143c. A non-inverting input terminal of the comparator 143a receives the output signal of the integrator 142. An inverting input terminal of the comparator 143a is connected to a slidable contact in the variable resistor 143b. One end of the variable resistor 143b is connected to the positive terminal of the battery 143c. The other end of the variable resistor 143b is grounded. The negative terminal of the battery 143c is also grounded. The variable resistor 143b and the battery 143c cooperate to apply a first reference voltage to the inverting input terminal of the comparator 143a. The first reference voltage depends on the position of the slidable contact in the variable resistor 143b. The first reference voltage is pre-adjusted into correspondence with a lower limit Imin for the integration result value Ip related to the burning ion current. The device 143a compares the output signal of the integrator 142 with the first reference voltage. In other words, the device 143a compares the integration result value Ip with the lower limit Imin. When the voltage of the output signal of the integrator 142 is equal to or higher than the first reference voltage, that is, when the integration result value Ip is equal to or greater than the lower limit Imin, the comparator 143a outputs an H-level signal. When the voltage of the output signal of the integrator 142 is lower than the first reference voltage, that is, when the integration result value Ip is smaller than the lower limit Imin, the comparator 143a outputs an L-level signal.

In the ion-current processing circuit 140, the first output judgment circuit 143 is followed by an ECU 144 for misfire detection. The ECU 144 includes, for example, a microcomputer or a similar device. The ECU 144 receives the output signal of the comparator 143a in the first output judgment circuit 143. The ion-current processing circuit 140 includes an inverter 144A via which the ECU 144 is connected to the ECU 130. The inverter 144A receives the gate control signal SG2 from the ECU 130. The inverter 144A provides an inversion of the gate control signal SG2.

The ECU 144 receives the inversion of the gate control signal SG2 from the inverter 144A. The ECU 144 detects the logic level of the output signal of the comparator 143a at every given timing determined by the inversion of the gate control signal SG2. When the detected logic level of the output signal of the comparator 143a is equal to an L level, the ECU 144 decides that the combustion chamber of the engine is in a misfire state. When the detected logic level of the output signal of the comparator 143a is equal to an H level, the ECU 144 decides that the combustion chamber of the engine is out of the misfire state.

In the ion-current processing circuit 140, the high pass filter 145 receives the output signal of the low pass filter 141. The high pass filter 145 removes low-frequency components from the output signal of the low pass filter 141. The high pass filter 145 is designed to extract components from the output signal of the low pass filter 141 which have knock-related frequencies at and around, for example, 7 kHz. Thus, the high pass filter 145 serves as a knock component extracting means. The cutoff frequency of the high pass filter 145 is set to, for example, 6 kHz. Components of the ion-current signal which pass through the low pass filter 141 and the high pass filter 145 have frequencies in the range of, for example, 6 to 8 kHz.

In the ion-current processing circuit 140, the high pass filter 145 is followed by a peak hold circuit 146 which serves as a maximum amplitude detecting means. The peak hold circuit 146 is connected to the ECU 130. The peak hold circuit 146 receives the gate control signal SG2 from the ECU 130. The device 146 holds a maximum amplitude of the output signal of the high pass filter 145 which occurs during every given time interval (or every given crank angle interval) determined by the gate control signal SG2. Thus, the device 146 holds a peak amplitude value (a peak voltage) ΔIp of the output signal of the high pass filter 145. The peak hold circuit 146 outputs a signal representing the held peak value ΔIp. The output signal of the peak hold circuit 146, that is, the held peak value, is updated or reset at every given timing determined by the gate control signal SG2.

In the ion-current processing circuit 140, the peak hold circuit 146 is followed by a second output judgment circuit 147. The second output judgment circuit 147 includes a comparator 147a, a variable resistor 147b, and a battery 147c. A non-inverting input terminal of the comparator 147a receives the output signal of the peak hold circuit 146. An inverting input terminal of the comparator 147a is connected to a slidable contact in the variable resistor 147b. One end of the variable resistor 147b is connected to the positive terminal of the battery 147c. The other end of the variable resistor 147b is grounded. The negative terminal of the battery 147c is also grounded. The variable resistor 147b and the battery 147c cooperate to apply a second reference voltage to the inverting input terminal of the comparator 147a. The second reference voltage depends on the position of the slidable contact in the variable resistor 147b. The second reference voltage is pre-adjusted into agreement with a given knock judgment level ΔImax. The device 147a compares the output signal of the peak hold circuit 146 with the second reference voltage. In other words, the device 147a compares the peak value ΔIp of the knock-frequency components with the knock judgment level ΔImax. When the voltage of the output signal of the peak hold circuit 146 is equal to or higher than the second reference voltage, that is, when the peak value ΔIp is equal to or greater than the knock judgment level ΔImax, the comparator 147a outputs an H-level signal. When the voltage of the output signal of the peak hold circuit 146 is lower than the second reference voltage, that is, when the peak value ΔIp is smaller than the knock judgment level ΔImax, the comparator 147a outputs an L-level signal.

In the ion-current processing circuit 140, the second output judgment circuit 147 is followed by an ECU 148 for knock detection. The ECU 148 includes, for example, a microcomputer or a similar device. The ECU 148 receives the output signal of the comparator 147a in the second output judgment circuit 147. The ion-current processing circuit 140 includes an inverter 148A via which the ECU 148 is connected to the ECU 130. The inverter 148A receives the gate control signal SG2 from the ECU 130. The inverter 148A provides an inversion of the gate control signal SG2. The ECU 148 receives the inversion of the gate control signal SG2 from the inverter 148A. The ECU 148 detects the logic level of the output signal of the comparator 147a at every given timing determined by the inversion of the gate control signal SG2. When the detected logic level of the output signal of the comparator 147a is equal to an H level, the ECU 148 decides that the combustion chamber of the engine is in a knocking state. When the detected logic level of the output signal of the comparator 147a is equal to an L level, the ECU 148 decides that the combustion chamber of the engine is out of the knocking state.

It is preferable that the ECU 144 informs the ECU 130 of the misfire detection result, and the ECU 148 informs the ECU 130 of the knock detection result. In this case, when the misfire detection result and the knock detection result indicate that the combustion chamber of the engine is out of the misfire state and the knocking state, the ECU 130 decides that the combustion chamber is in a normally operating state. Otherwise, the ECU 130 decides that the combustion chamber is in a wrong state. The ECU 144 and the ECU 148 correspond to a burning condition detecting means.

Operation of the apparatus of FIG. 10 will be described with reference to FIGS. 11–14. As shown in the portion (A) of FIG. 11, at a moment t1, the spark control signal IGT changes from the L level to the H level. The spark control signal IGT continues to be in the H-level state until a subsequent moment t2. At the moment t2, the spark control signal IGT returns from the H level to the L level. At the moment t2 and also immediately after the moment t2, electrostatic energy applied to the spark plug 110 causes a capacitance discharge between the opposed electrodes 111 and 112 of the spark plug 110. An induced discharge follows the capacitance discharge. The induced discharge is caused by electromagnetic energy fed from the transformer 121 to the spark plug 110. The capacitance discharge and the induced discharge ignite an air-fuel mixture in the combustion chamber of the engine. Thus, the air-fuel mixture starts to burn. Therefore, as shown in the portion (C) of FIG. 11, the pressure in the combustion chamber of the engine (that is, the cylinder pressure) starts to rise after the moment t2.

Figure 11:
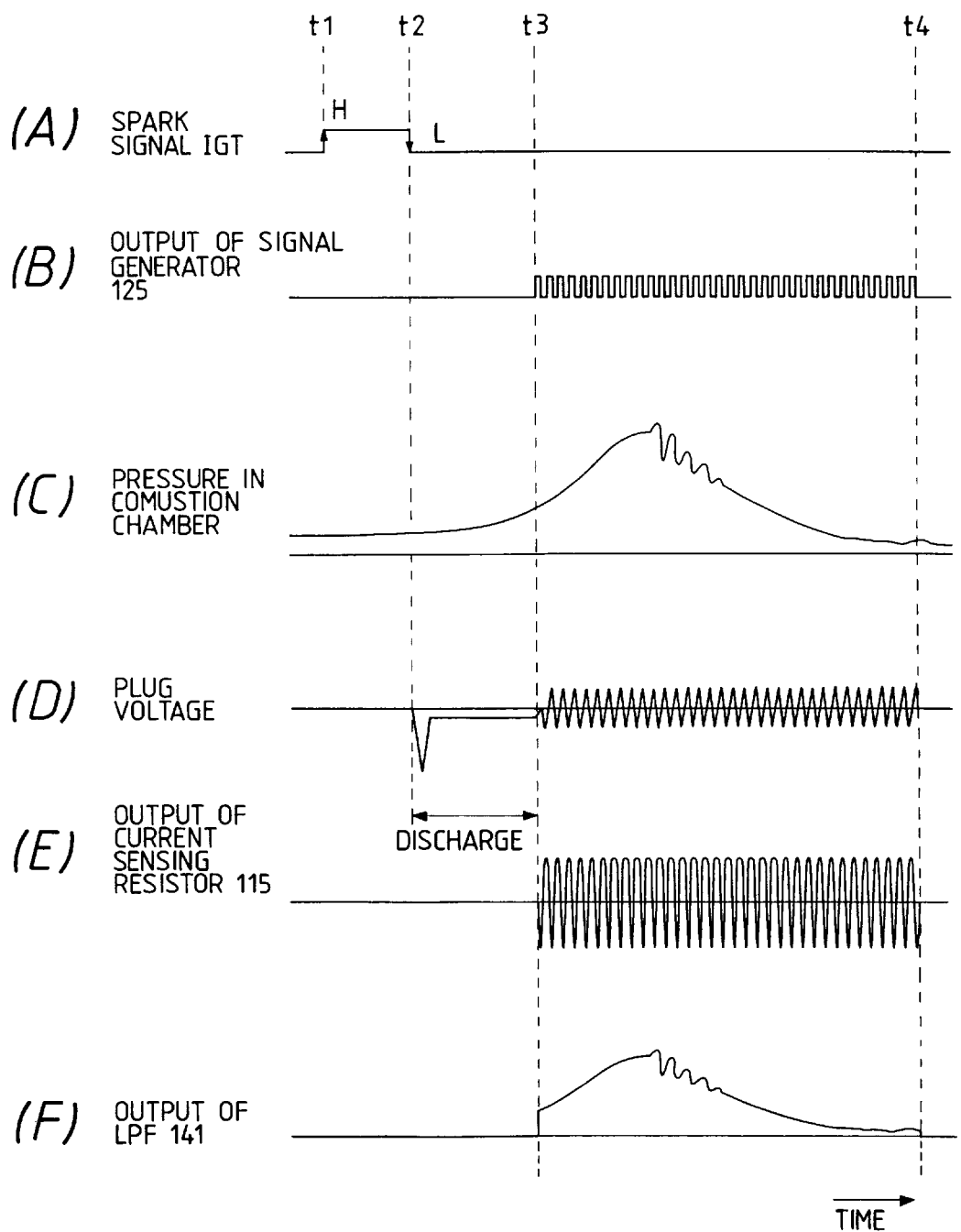
FIG. 11 is a time-domain diagram of various signals and a cylinder pressure in the apparatus of FIG. 10.

As shown in the portion (B) of FIG. 11, at a moment t3 subsequent to the moment t2, the signal generator 125 starts to output the rectangular wave signal in response to the gate control signal SG2. The signal generator 125 continues to output the rectangular wave signal until a moment t4 following the moment t3. At the moment t4, the signal generator 125 stops outputting the rectangular wave signal in response to the gate control signal SG2. The time interval between the moments t3 and t4 is chosen to be within a time interval during which the air-fuel mixture continues to burn.

The rectangular wave signal outputted from the signal generator 125 travels to the base of the switching transistor 123 via the OR gate 124. The switching transistor 123 periodically changes between the on state and the off state in response to the rectangular wave signal so that an alternating current having a frequency equal to the frequency of the rectangular wave signal flows through the primary winding 121a of the transformer 121. A high alternating voltage (high AC voltage) corresponding to the alternating current in the primary winding 121a is induced across the secondary winding 121b of the transformer 121. Therefore, during the time interval between the moments t3 and t4, the high alternating voltage which corresponds to the rectangular wave signal remains applied between the opposed electrodes 111 and 112 of the spark plug 110 as shown in the portion (D) of FIG. 11.

As shown in the portion (E) of FIG. 11, during the time interval between the moments t3 and t4, an AC signal voltage appears across the fixed resistor 115. The AC signal voltage has low-frequency or DC components related to the pressure (or the ion current) in the combustion chamber of the engine and high-frequency components unrelated to the pressure (or the ion current) in the combustion chamber of the engine. The low pass filter 141 receives the AC signal voltage from the fixed resistor 115. The low pass filter 141 removes the high-frequency components from the AC signal voltage, and thereby converts the AC signal voltage into an accurate ion-current signal. As shown in the portion (F) of FIG. 11, the ion-current signal outputted from the low pass filter 141 reflects the pressure in the combustion chamber of the engine.

The high-frequency components removing function by the low pass filter 141 involves an integrating function. As shown in the portion (E) of FIG. 11, waveforms of positive portions of the AC signal voltage across the fixed resistor 115 significantly differ from those of negative portions thereof. Thus, an appreciable signal results from integration of the AC signal voltage by the low pass filter 141.

Operation of the low pass filter 141 will be described in more detail. As shown in the portion (A) of FIG. 12, the rectangular wave signal outputted from the signal generator 125 periodically changes between the H level and the L level. As shown in the portion (B) of FIG. 12, an AC voltage applied between the opposed electrodes 111 and 112 of the spark plug 110 periodically varies in response to the rectangular wave signal. The waveform of the AC voltage applied to the spark plug 110 is sinusoidal rather than rectangular due to the smoothing function of stray capacitances related to the switching transistor 123 and the transformer 121. The phase of the AC voltage applied to the spark plug 110 retards from the phase of the rectangular wave signal by about 90°. The AC voltage applied to the spark plug 110 causes a current to flow between the opposed electrodes 111 and 112 thereof. The current between the opposed electrodes 111 and 112 has a capacitive current component and a burning ion current component.

Figure 12:
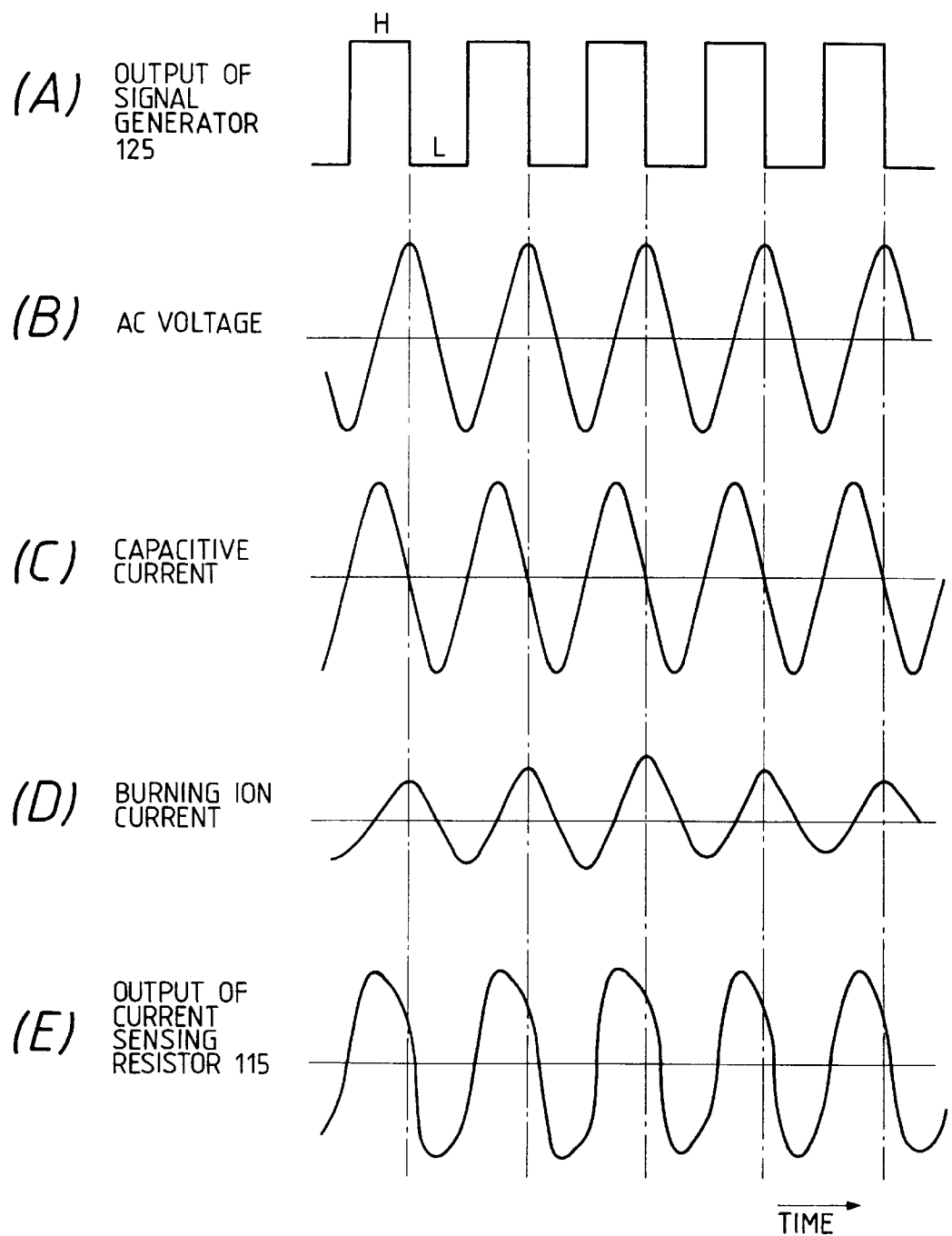
FIG. 12 is a time-domain diagram of various signals in the apparatus of FIG. 10.

As shown in the portion (C) of FIG. 12, the capacitive current component of the current between the opposed electrodes 11 1 and 112 of the spark plug 110 varies in a sinusoidal waveform. The capacitive current component corresponds to a time-based differential of the AC voltage applied to the spark plug 110. As shown in the portion (D) of FIG. 12, the burning ion current component of the current between the opposed electrodes 111 and 112 of the spark plug 110 varies in approximately a sinusoidal waveform. The amplitude of the burning ion current component increases as the amount or the density of ions caused by the burning increases. The burning ion current component is in phase with the AC voltage applied to the spark plug 110. The burning ion current component peaks at the moment of every change of the rectangular wave signal from the H level to the L level. The sum of the capacitive current component and the burning ion current component is detected as a current flowing through the fixed resistor 115.

As shown in the portion (E) of FIG. 12, the current through the fixed resistor 115 varies at a frequency equal to the frequency of the rectangular waveform signal. The signal voltage which appears across the fixed resistor 115 represents the current through the fixed resistor 115. The signal voltage is inputted into the low pass filter 141 from the fixed resistor 115. The signal voltage has a component related to the capacitive current and also a component related to the burning ion current. The low pass filter 141 subjects the signal voltage to an integrating process which separates the burning ion current component from the capacitive current component.

Figure 13:
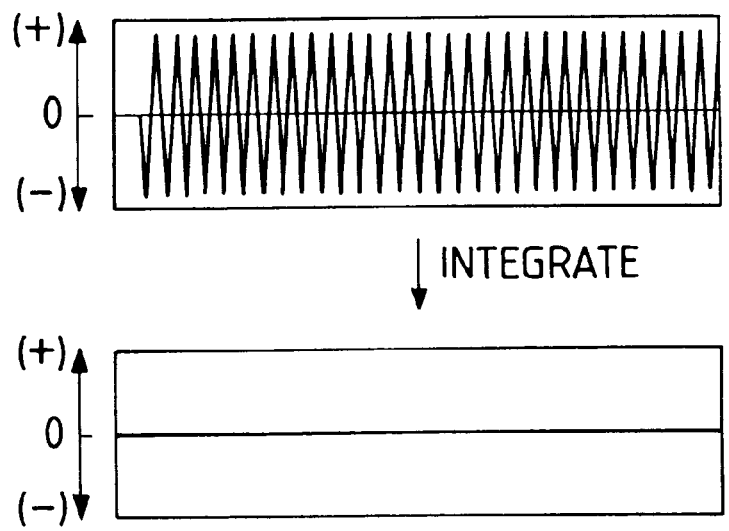
FIG. 13 is a diagram of signal waveforms in the apparatus of FIG. 10.

As shown in the upper portion of FIG. 13, the capacitive current component of the signal voltage alternates between a positive side and a negative side. The center level of the capacitive current component substantially agrees with a voltage of 0. Accordingly, the capacitive current component in the positive side and the capacitive current component in the negative side are canceled by the integrating function of the low pass filter 141. Thus, as shown in the lower portion of FIG. 13, the integral of the capacitive current component results in a voltage of 0 at the output terminal of the low pass filter 141.

Figure 14:
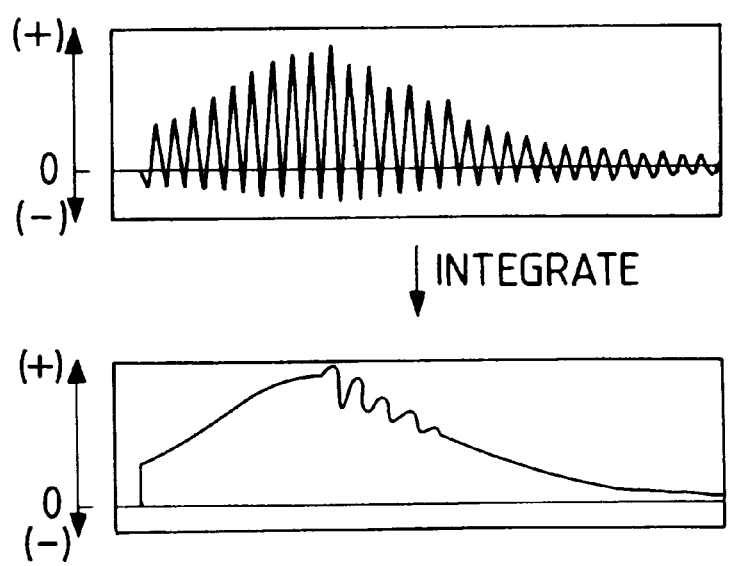
FIG. 14 is a diagram of signal waveforms in the apparatus of FIG. 10.

As shown in the upper portion of FIG. 14, the burning ion current component of the signal voltage alternates between a positive side and a negative side. The center level of the burning ion current component is offset from a voltage of 0 toward the positive side. Accordingly, only a small part of the burning ion current component in the positive side is canceled by the burning ion current component in the negative side during the integrating process by the low pass filter 141. Thus, as shown in the lower portion of FIG. 14, the integral of the burning ion current component results in an appreciable positive voltage at the output terminal of the low pass filter 141. The positive voltage is equal to the ion-current signal outputted from the low pass filter 141 (see the portion (F) of FIG. 11).

Figure 15:
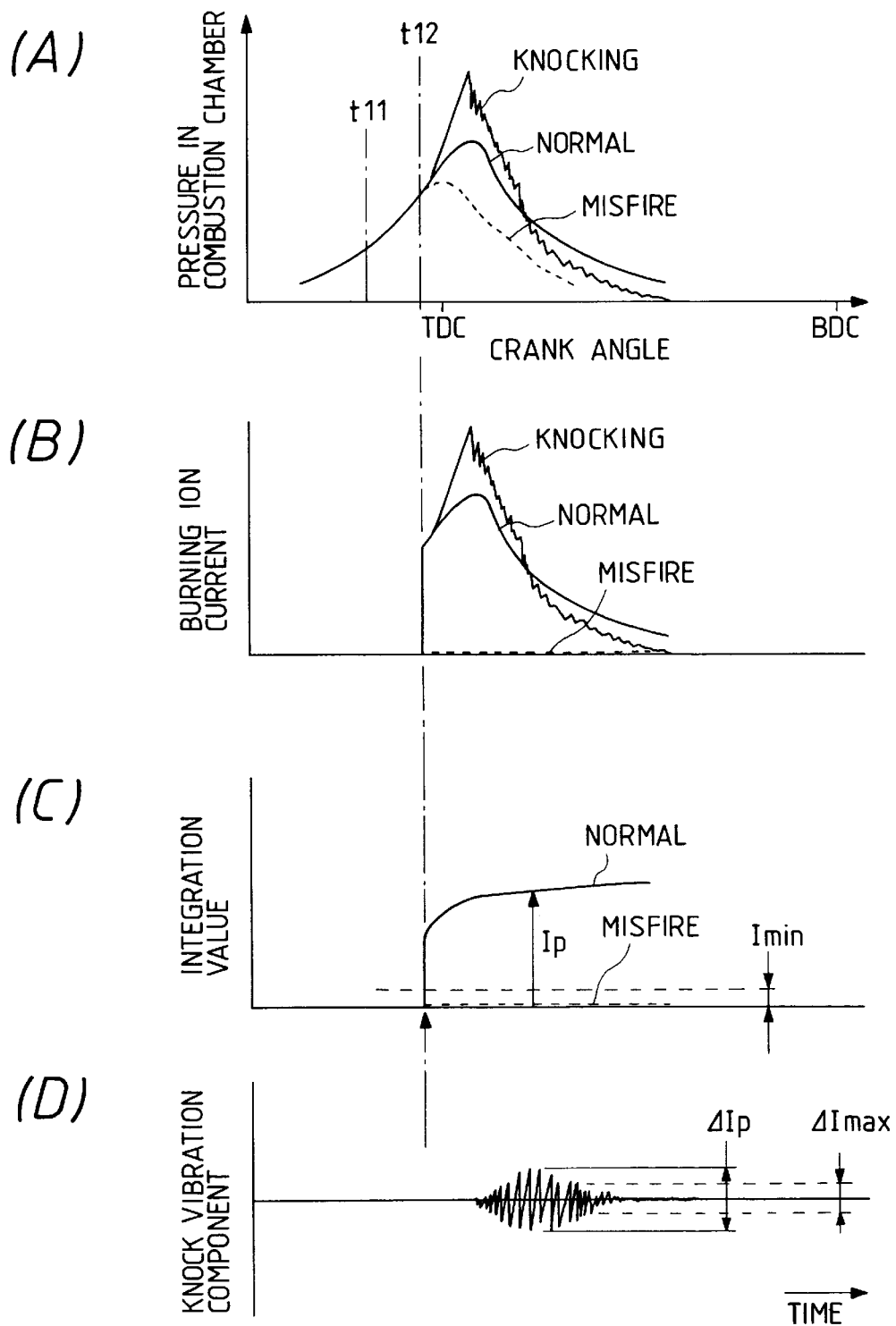
FIG. 15 is a time-domain diagram of various signals and a cylinder pressure in the apparatus of FIG. 10.

With reference to FIG. 15, an explanation will be given of the processing of the output signal of the low pass filter 141 to detect conditions of the burning in the combustion chamber of the engine. In FIG. 15, the character "t11" denotes a moment of the occurrence of ignition, and the character "t12" denotes a moment of the end of an induced discharge after the ignition.

The portion (A) of FIG. 15 shows examples of the time-domain variations in the pressure in the combustion chamber of the engine which occur under a normal burning condition, a knocking condition, and a misfire condition respectively. The pressure in the combustion chamber peaks at or immediately after a moment corresponding to a top dead center (TDC) under each of the normal burning condition, the knocking condition, and the misfire condition. In the knocking condition, pressure wave having frequencies at and around a certain frequency (a knock frequency) occurs, and a vibration component corresponding to the pressure wave is superimposed on the pressure in the combustion chamber. In the normal burning condition, such a knock vibration component is absent from the pressure in the combustion chamber. In the misfire condition, burning-related ions are not generated, and the pressure in the combustion chamber varies similarly to a pressure variation available in motoring or cranking operation of the engine.

The portion (B) of FIG. 15 shows examples of the time-domain variations in the burning ion current which occur under a normal burning condition, a knocking condition, and a misfire condition respectively. As previously explained, the burning ion current is represented by the output signal of the low pass filter 141. In the normal burning condition or the knocking condition, the variation in the burning ion current accurately corresponds to the variation in the pressure in the combustion chamber. Furthermore, in the knocking condition, a knock vibration is superimposed on the burning ion current. In the misfire condition, burning-related ions are not generated so that the burning ion current remains absent.

The portion (C) of FIG. 15 shows examples of the time-domain variations in the output signal of the integrator 142 which occur under a normal burning condition and a misfire condition respectively. Since the output signal of the integrator 142 represents the value Ip of the accumulation or the integral of the burning ion current, the output signal of the integrator 142 accurately corresponds to the degree of the burning in the normal burning condition. When the integration result value Ip represented by the output signal of the integrator 142 is smaller than the lower limit Imin, the ECU 144 decides that a misfire occurs in the combustion chamber of the engine. Thus, the misfire detection is implemented by referring to the output signal of the integrator 142. The misfire detection of this type is less affected by a variation from burning to burning. Accordingly, the misfire detection of this type is accurate.

The portion (D) of FIG. 15 shows an example of the time-domain variation in the output signal of the high pass filter 145 which occurs under a knocking condition. The low pass filter 145 extracts a knock vibration component from the output signal of the low pass filter 141. The peak amplitude value ΔIp of the extracted knock vibration component is equal to or higher than the knock judgment level ΔImax, the ECU 148 decides that a knocking occurs in the combustion chamber of the engine.

The apparatus of FIG. 10 has the following advantages. As previously explained, the low pass filter 141 removes the capacitive current component from the signal voltage generated by the fixed resistor 115, and hence extracts only the burning ion current component therefrom. Thus, the ion current can be accurately detected. Generally, the low pass filter 141 is simple in structure. As previously explained, the output signal of the low pass filter 141 is processed by the integrator 142, and the judgment as to a misfire is implemented on the basis of the integration result provided by the integrator 142. Thus, the occurrence of a misfire can be reliably detected. As previously explained, the high pass filter 145 extracts a knock-related component from the output signal of the low pass filter 141, and the peak hold circuit 146 detects a peak amplitude value ΔIp of the output signal of the high pass filter 145. The judgment as to knocking is implemented on the basis of the detected peak amplitude value ΔIp. Thus, the occurrence of a knocking can be reliably detected.

Sixth Embodiment

Figure 16:
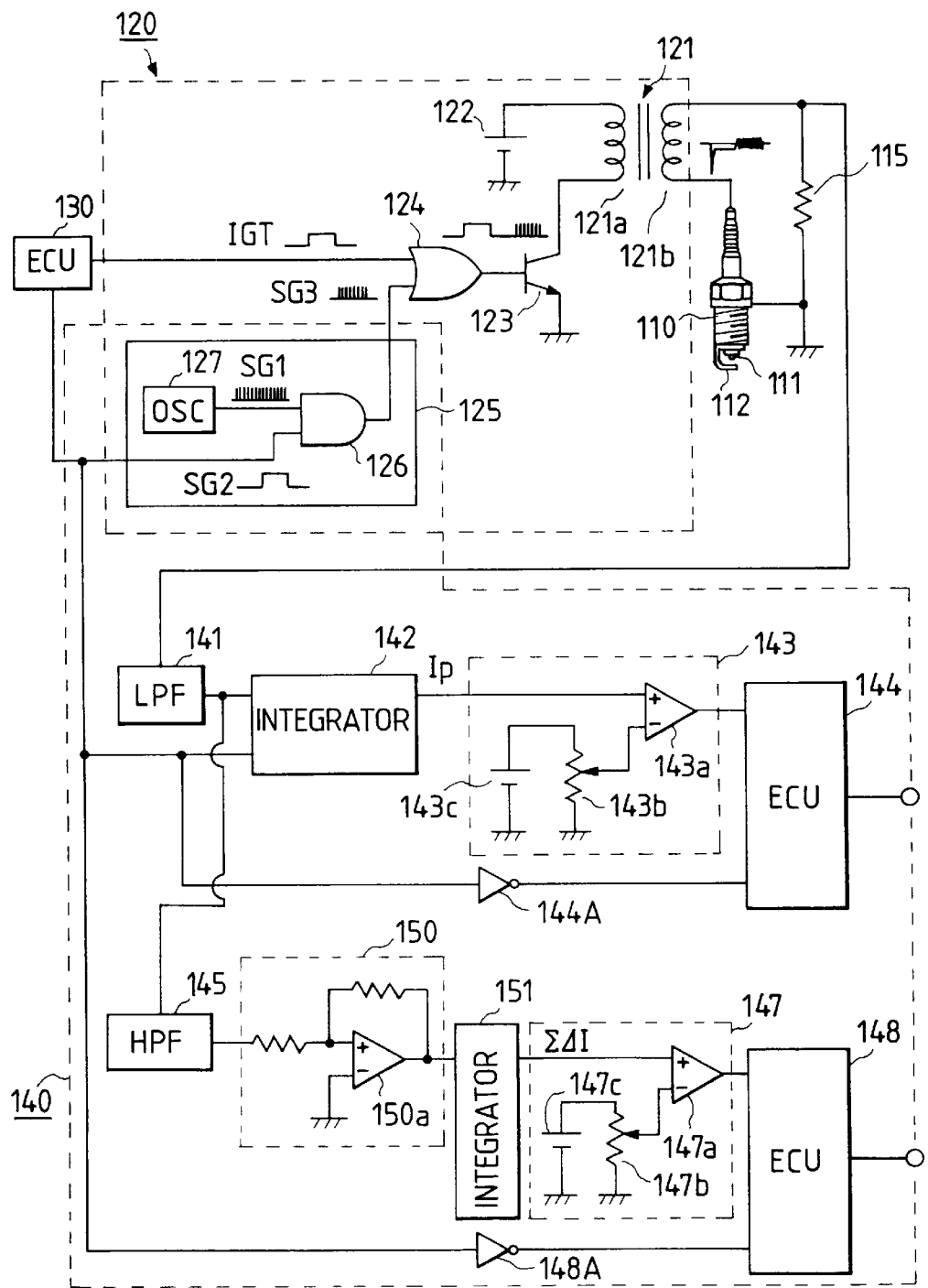
FIG. 16 is a diagram of an apparatus for detecting a condition of burning in an internal combustion engine according to a sixth embodiment of this invention.

FIG. 16 shows a sixth embodiment of this invention which is similar to the embodiment of FIG. 10 except that a half-wave rectifier 150 and an integrator 151 replace the peak hold circuit 146 (see FIG. 10).

In the embodiment of FIG. 16, a high pass filter 145 is successively followed by the half-wave rectifier 150, the integrator 151, and a second output judgment circuit 147. The half-wave rectifier 150 includes an operational amplifier 150a. A non-inverting input terminal of the operational amplifier 150a is connected to the output terminal of the high pass filter 145. An inverting input terminal of the operational amplifier 150a is grounded. The output terminal of the operational amplifier 150a is connected to the input terminal of the integrator 151. The output terminal of the integrator 151 is connected to a non-inverting input terminal of a comparator 147a in the second output judgment circuit 147.

The output signal of the high pass filter 145 is subjected by the device 150 to half-wave rectification. The resultant output signal of the half-wave rectifier 150 is integrated by the device 151. The output signal of the integrator 151 represents the value ΣΔI of the result of the integration. The output signal of the integrator 151 is applied to the non-inverting input terminal of the comparator 147a in the second output judgment circuit 147.

In the second output judgment circuit 147, a variable resistor 147b and a battery 147c cooperate to apply a second reference voltage to the inverting input terminal of the comparator 147a. The second reference voltage depends on the position of the slidable contact in the variable resistor 147b. The second reference voltage is pre-adjusted into agreement with a given knock judgment level ΣΔImax. The device 147a compares the integration result value ΣΔI with the knock judgment level ΣΔImax. When the integration result value ΣΔI is equal to or greater than the knock judgment level ΣΔImax, the comparator 147a outputs an H-level signal. When the integration result value ΣΔI is smaller than the knock judgment level ΣΔImax, the comparator 147a outputs an L-level signal.

The second output judgment circuit 147 is followed by an ECU 148 for knock detection. The ECU 148 receives the output signal of the comparator 147a in the second output judgment circuit 147. The ECU 148 detects the logic level of the output signal of the comparator 147a at every given timing determined by the inversion of a gate control signal SG2. When the detected logic level of the output signal of the comparator 147a is equal to an H level, the ECU 148 decides that the combustion chamber of the engine is in a knocking state. When the detected logic level of the output signal of the comparator 147a is equal to an L level, the ECU 148 decides that the combustion chamber of the engine is out of the knocking state.

Seventh Embodiment

Figure 17:
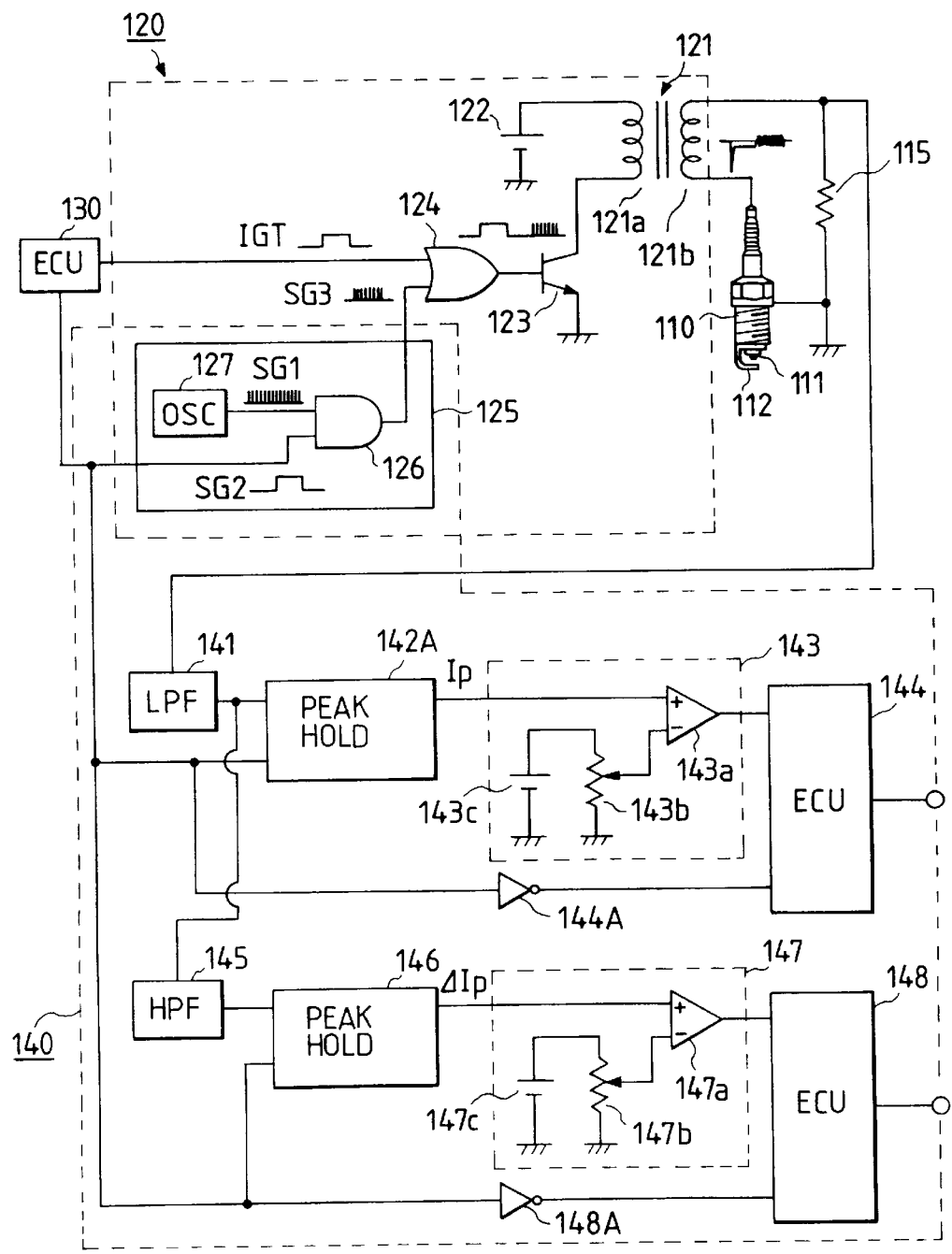
FIG. 17 is a diagram of an apparatus for detecting a condition of burning in an internal combustion engine according to a seventh embodiment of this invention.

FIG. 17 shows a seventh embodiment of this invention which is similar to the embodiment of FIG. 10 except that a peak hold circuit 142A replaces the integrator 142 (see FIG. 10). The peak hold circuit 142A corresponds to a peak value detecting means.

In the embodiment of FIG. 17, the device 142A detects a peak level of the output signal of a low pass filter 141. A comparator 143a in a first output judgment circuit 143 compares the peak level detected by the peak hold circuit 142A with a reference voltage. An ECU 144 for misfire detection decides that a combustion chamber of an engine is in a misfire state when the peak level detected by the peak hold circuit 142A is lower than the reference voltage.

Eighth Embodiment

Figure 18:
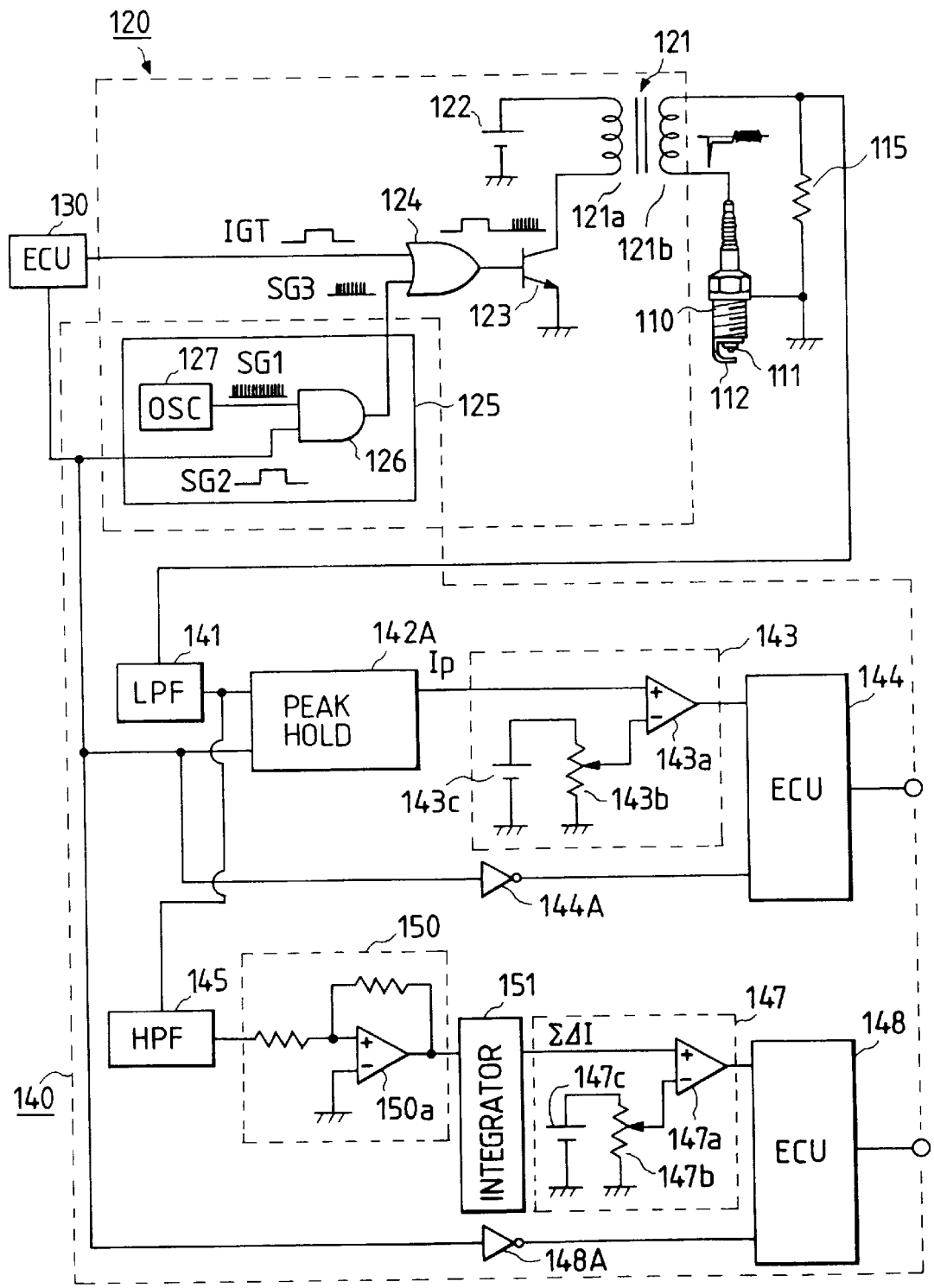
FIG. 18 is a diagram of an apparatus for detecting a condition of burning in an internal combustion engine according to an eighth embodiment of this invention.

FIG. 18 shows an eighth embodiment of this invention which is similar to the embodiment of FIG. 16 except that a peak hold circuit 142A replaces the integrator 142 (see FIG. 16). The peak hold circuit 142A corresponds to a peak value detecting means.

In the embodiment of FIG. 18, the device 142A detects a peak level of the output signal of a low pass filter 141. A comparator 143a in a first output judgment circuit 143 compares the peak level detected by the peak hold circuit 142A with a reference voltage. An ECU 144 for misfire detection decides that a combustion chamber of an engine is in a misfire state when the peak level detected by the peak hold circuit 142A is lower than the reference voltage.

Other Embodiments

The embodiments of FIGS. 10, 16, 17, and 18 may be modified as follows. A first modification of the embodiments of FIGS. 10, 16, 17, and 18 uses an integrator in place of the low pass filter 141 (see FIGS. 10, 16, 17, and 18). The used integrator includes, for example, a CR circuit. A second modification of the embodiments of FIGS. 10, 16, 17, and 18 uses a microcomputer in place of the ion-current processing circuit 140 (see FIGS. 10, 16, 17, and 18). In this case, the microcomputer is programmed to implement signal processing similar to the signal processing by the ion-current processing circuit 140. A third modification of the embodiments of FIGS. 10, 16, 17, and 18 uses an exclusive ion probe in place of the spark plug 110 (see FIGS. 10, 16, 17, and 18). The exclusive ion probe has a pair of opposed electrodes. According to a fourth modification of the embodiments of FIGS. 10, 16, 17, and 18, the ECU 130, the ECU 144, and the ECU 148 are formed by a common ECU. In this case, the common ECU is programmed to implement signal processings corresponding to the ECU 130, the ECU 144, and the ECU 148 on a time division basis. The knock detection part may be omitted from each of the embodiments of FIGS. 10, 16, 17, and 18. The misfire detection part may be omitted from each of the embodiments of FIGS. 10, 16, 17, and 18.

What is claimed is:

1. An apparatus for detecting a burning condition, comprising:

a pair of opposed electrodes provided in a combustion chamber of an internal combustion engine;

an AC voltage source that applies an AC voltage between the pair of opposed electrodes, the AC voltage being used for detection of an ion current;

a current detector that detects a current flowing between the opposed electrodes, and outputs a current representing signal containing an AC current component associated with the AC voltage and a burning ion current component; and an ion current component detector that detects the ion current component by eliminating the AC current component from the current detected by the current detector.

2. The apparatus of claim 1, wherein the ion current component detector comprises a detected current controller that outputs the current-representing signal at a given phase with respect to the AC voltage.

3. The apparatus of claim 2, wherein the detected current controlling means comprises a voltage trigger generating circuit for generating a trigger at a given phase with respect to the AC voltage, and a sample-and-hold circuit for latching the current-representing signal when the trigger is generated, the sample-and-hold circuit outputting a burning-ion-current representing signal.

4. The apparatus of claim 1, wherein the ion current component detector comprises a phase difference detector that detects a phase difference between the AC voltage and the current-representing signal, and for outputting a burning-ion-current representing signal in response to the detected phase difference.

5. The apparatus of claim 4, wherein the phase difference detecting means comprises a first phase trigger generating circuit for generating a first trigger at a given phase with respect to the AC voltage, a second phase trigger generating circuit for generating a second trigger when the current-representing signal reaches a given level, and a time measuring circuit for measuring a time from a moment of occurrence of the first trigger to a moment of occurrence of the second trigger, the measured time being the detected phase difference.

6. The apparatus of claim 1, wherein the ion current component detector comprises an AC current generator that generates an AC current representing signal having a given phase with respect to the AC voltage, and a subtracting circuit that generates the ion current component generating signal corresponding to a difference between the AC current representing signal and the current detected by the current detector.

7. The apparatus of claim 6, further comprising calculating means for calculating a ratio between a parameter represented by the burning-ion-current representing signal and a parameter represented by a signal depending on the AC voltage applied between the opposed electrodes.

8. The apparatus of claim 1, wherein the ion current component detector comprises a differentiating circuit for differentiating the AC voltage into the AC current representing signal.

9. The apparatus of claim 8, further comprising calculating means for calculating a ratio between a parameter represented by the burning-ion-current representing signal and a parameter represented by a signal depending on the AC voltage applied between the opposed electrodes.

10. An apparatus according to claim 1, wherein the ion current component detector comprises a low pass filter which passes a lower frequency signal in the current detected by the current detector than the AC voltage frequency.

11. The apparatus of claim 1, wherein said voltage applying means comprises a signal generator, a switching transistor, and a transformer.

12. An apparatus according to claim 1, said ion current component detector comprising an integrator that integrates the current flowing in the opposite electrodes to eliminate the AC current component associated with the AC voltage from the current detected by the current detector to detect the ion current component.

13. An apparatus according to claim 12, wherein the integrator includes an integrator which integrates the current-representing signal during a predetermined interval, and the apparatus further comprises a detector that detects a misfire in the combustion chamber when a value of a result of the integrating by the integrator is below a predetermined reference value.

14. An apparatus according to claim 12, further comprising a peak value detector that detects a peak value of the current-representing signal, and a detector that detects a misfire in the combustion chamber when the peak value detected by the peak value detector is below a predetermined reference value.

15. An apparatus according to claim 12, further comprising:
a knock component filter that filters a knock-related component from the current-representing signal, the knock-related component having a predetermined frequency corresponding to a knocking;
a maximum amplitude detector that detects a maximum value of an amplitude of the knock-related component filtered by the knock component filter; and
a combustion chamber knocking state detector that detects a knocking state when the maximum value detected by the maximum amplitude detector is equal to or greater than a predetermined reference value.

16. An apparatus according to claim 15, wherein the knock component filter comprises a high pass filter.

17. An apparatus according to claim 12, further comprising:
a knock component filter that filters a knock-related component from the current-representing signal, the knock-related component having a predetermined frequency corresponding to a knocking;
a half-wave rectifier for half wave-rectifying the knock-related component filtered by the knock component filter during a predetermined interval;
an integrator for integrating an output signal of the half-wave rectifier; and
a combustion chamber knocking state detector that detects a knocking state when a value of a result of the integrating by the integrator is equal to or greater than a predetermined reference value.

18. An apparatus according to claim 17, wherein the knock component filter comprises a high pass filter.

19. An apparatus for detecting a condition for burning, comprising:
a pair of opposed electrodes provided in a combustion chamber of an internal combustion engine;
an AC voltage source that supplies an AC voltage between the pair of opposed electrodes, the AC voltage source being used for detection of an ion current;
a current detector that detects a current flowing between the pair of opposed electrodes, and outputs a current representing signal depending on the detected current, said current-representing signal containing an AC current component associated with the AC voltage and a burning ion current component; and
a sampling element that samples the current representing signal when the AC current component is at a null during the detection of the current to effectively eliminate the AC current component from the current representing signal and thereby extract the burning ion current from the current representing signal, the AC current component occurring in correspondence with the AC voltage, the burning ion current component corresponding to a burning ion current which flows between the opposed electrodes.

20. An apparatus for detecting a burning condition in an internal combustion engine, comprising:
a pair of opposed electrodes provided in a combustion chamber;
an oscillator capable of producing a rectangular wave signal;
a transistor receiving the rectangular wave signal, said transistor having an emitter-collector path which is periodically made conductive and non-conductive in response to the rectangular wave signal;
a transformer having a primary winding connected to an output of the transistor, the transistor and transformer producing an AC voltage across the opposed electrodes, said AC voltage occurring in response to the smoothing effects on the rectangular wave signal of stray capacitances;
a current detecting circuit capable of detecting a current flowing between said pair of opposed electrodes, said detected current comprising an AC current component and a burning ion current component; and
a circuit capable of eliminating the AC current component from said detected current.

21. The apparatus of claim 20, wherein said eliminating circuit comprises a detected current controlling circuit which samples the detected current at a given phase with respect to the phase of the AC voltage.

22. An apparatus according to claim 20, wherein said detected current controlling circuit samples the detected current at the descending edge of the rectangular signal, said apparatus further comprising:
a sample-and-hold circuit for latching the detected current when said detected current controlling circuit samples the detected current to effectively eliminate the AC current component from the detected current.

* * * * *